(12) United States Patent
Zimmerman

(10) Patent No.: US 6,951,647 B2
(45) Date of Patent: Oct. 4, 2005

(54) T CELL BINDING LIGAND PEPTIDES AND METHOD OF INDUCING A CELLULAR IMMUNE RESPONSE

(75) Inventor: Daniel H. Zimmerman, Bethesda, MD (US)

(73) Assignee: Cel-Sci Corporation, Vienna, VA (US)

(*) Notice: Subject to any disclaimer, the term of this patent is extended or adjusted under 35 U.S.C. 154(b) by 256 days.

(21) Appl. No.: 10/296,317

(22) PCT Filed: May 24, 2001

(86) PCT No.: PCT/US01/16793

§ 371 (c)(1),
(2), (4) Date: Nov. 22, 2002

(87) PCT Pub. No.: WO01/89286

PCT Pub. Date: Nov. 29, 2001

(65) Prior Publication Data

US 2004/0057968 A1 Mar. 25, 2004

(51) Int. Cl.⁷ .............................................. A61K 39/00

(52) U.S. Cl. .............................. 424/192.1; 424/185.1; 424/193.1; 424/196.11; 424/278.1; 530/324; 530/326; 530/350; 530/403

(58) Field of Search ............................ 530/324, 326, 530/350, 403; 424/185.1, 192.1, 193.1, 196.11, 278.1

*Primary Examiner*—Jeffrey Stucker
(74) *Attorney, Agent, or Firm*—Sherman & Shalloway

(57) ABSTRACT

The present invention is based, in part, on the discovery that a modified version of Peptide G (Asn Gly Gln Glu Glu Lys Ala Gly Val Val Ser Thr Gly Leu Ile—SEQ ID NO:2) obtained by replacing Asn with Asp to form Peptide G' (Asp Gly Gln Glu Glu Lys Ala Gly Val Val Ser Thr Gly Leu Ile—SEQ ID NO: 1) overcomes the long range stabilization problem of the peptide conjugates and, quite surprisingly, also enhances the immune response, particularly the CD4 related (cell mediated) response, of conjugated peptides (L.E.A.P.S. constructs) as previously described.

9 Claims, 2 Drawing Sheets

Figure 1:
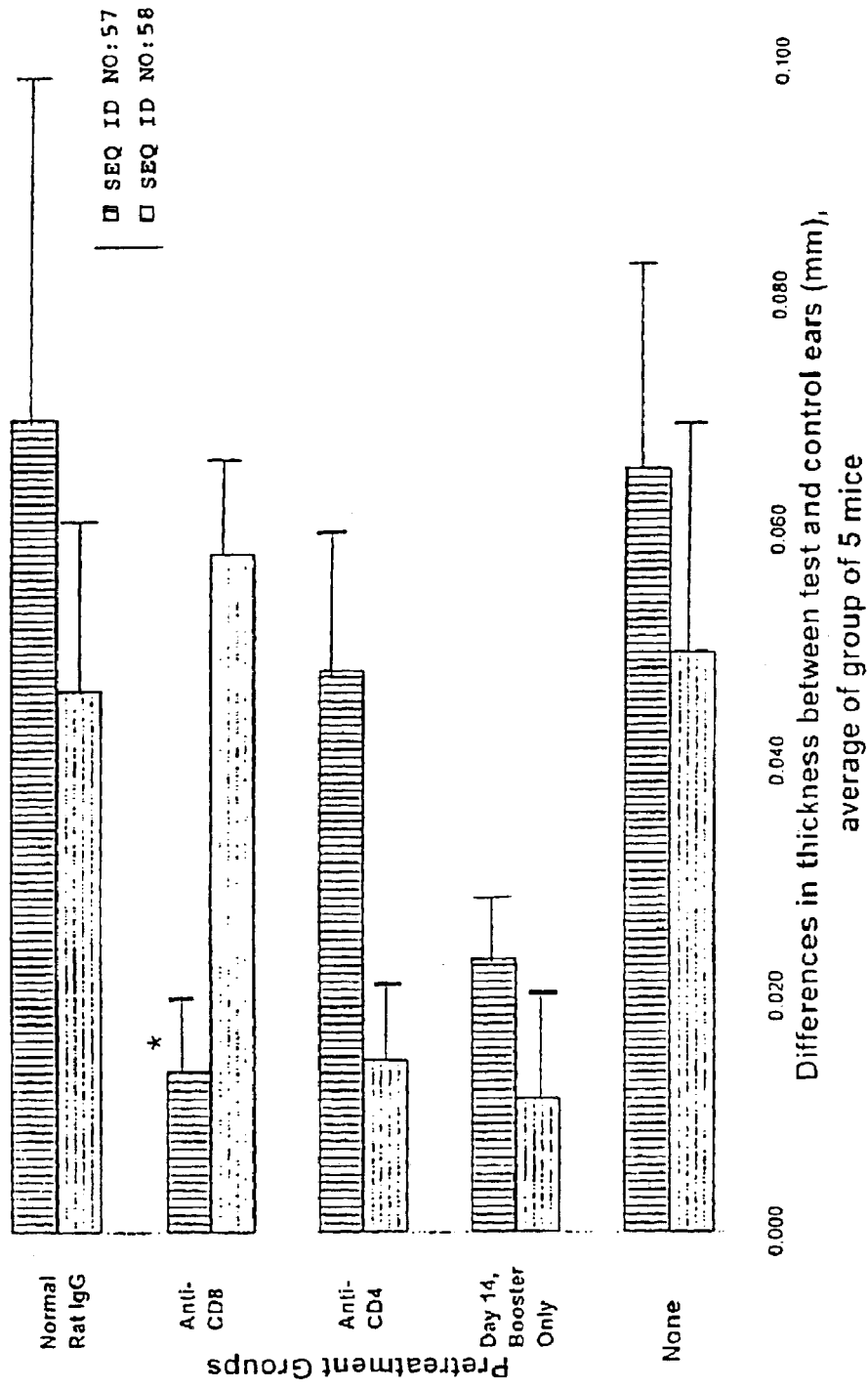

SEQUENCE LISTING

<160> NUMBER OF SEQ ID NOS: 96

<210> SEQ ID NO 1
<211> LENGTH: 15
<212> TYPE: PRT
<213> ORGANISM: Artificial Sequence
<220> FEATURE:
<223> OTHER INFORMATION: Peptide G'
<220> FEATURE:
<221> NAME/KEY: MOD_RES
<222> LOCATION: (15)..(15)
<223> OTHER INFORMATION: Amidation generally at the C-terminal of
      peptide

<400> SEQUENCE: 1

Asp Gly Gln Glu Glu Lys Ala Gly Val Val Ser Thr Gly Leu Ile
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Peptide G', a portion of the MHC II Beta chain
      residues from 135-149

<400> SEQUENCE: 2

Asn Gly Gln Glu Glu Lys Ala Gly Val Val Ser Thr Gly Leu Ile
1               5                   10                  15

<210> SEQ ID NO 3
<211> LENGTH: 25
<212> TYPE: PRT
<213> ORGANISM: Artificial Sequence
<220> FEATURE:
<223> OTHER INFORMATION: Peptide construct

<400> SEQUENCE: 3

Ala Thr Leu Tyr Ser Val His Gln Arg Ile Asp Val Lys Asp Thr Lys
1               5                   10                  15

Glu Ala Leu Glu Lys Ile Glu Glu Glu
            20                  25

<210> SEQ ID NO 4
<211> LENGTH: 36
<212> TYPE: PRT
<213> ORGANISM: Artificial Sequence
<220> FEATURE:
<223> OTHER INFORMATION: Peptide construct

<400> SEQUENCE: 4

Ser Leu Tyr Asn Thr Val Ala Thr Leu Tyr Ser Val His Gln Arg Ile
1               5                   10                  15

Asp Val Lys Asp Thr Lys Glu Ala Leu Glu Lys Ile Glu Glu Glu Gln
            20                  25                  30

Asn Lys Ser Lys
        35

<210> SEQ ID NO 5
<211> LENGTH: 37
<212> TYPE: PRT
<213> ORGANISM: Artificial Sequence
<220> FEATURE:
<223> OTHER INFORMATION: Peptide construct

```
<400> SEQUENCE: 5

Arg Ser Leu Tyr Asn Thr Val Ala Thr Leu Tyr Ser Val His Gln Arg
1               5                   10                  15

Ile Asp Val Lys Asp Thr Lys Glu Ala Leu Glu Lys Ile Glu Glu Glu
            20                  25                  30

Gln Asn Lys Ser Lys
        35

<210> SEQ ID NO 6
<211> LENGTH: 29
<212> TYPE: PRT
<213> ORGANISM: Artificial Sequence
<220> FEATURE:
<223> OTHER INFORMATION: Peptide construct

<400> SEQUENCE: 6

Ala Thr Leu Tyr Ser Val His Gln Arg Ile Asp Val Lys Asp Thr Lys
1               5                   10                  15

Glu Ala Leu Glu Lys Ile Glu Glu Glu Gln Asn Lys Ser
            20                  25

<210> SEQ ID NO 7
<211> LENGTH: 37
<212> TYPE: PRT
<213> ORGANISM: Artificial Sequence
<220> FEATURE:
<223> OTHER INFORMATION: Peptide construct

<400> SEQUENCE: 7

Lys Ser Leu Phe Asn Thr Val Ala Thr Leu Tyr Cys Val His Gln Arg
1               5                   10                  15

Ile Asp Val Lys Asp Thr Lys Glu Ala Leu Asp Lys Ile Glu Glu Ile
            20                  25                  30

Gln Asn Lys Ser Lys
        35

<210> SEQ ID NO 8
<211> LENGTH: 37
<212> TYPE: PRT
<213> ORGANISM: Artificial Sequence
<220> FEATURE:
<223> OTHER INFORMATION: Peptide construct

<400> SEQUENCE: 8

Arg Ser Leu Tyr Asn Thr Val Ala Thr Leu Tyr Cys Val His Gln Arg
1               5                   10                  15

Ile Glu Val Lys Asp Thr Lys Glu Ala Leu Asp Lys Ile Glu Glu Glu
            20                  25                  30

Gln Asn Lys Ser Lys
        35

<210> SEQ ID NO 9
<211> LENGTH: 37
<212> TYPE: PRT
<213> ORGANISM: Artificial Sequence
<220> FEATURE:
<223> OTHER INFORMATION: Peptide construct
<220> FEATURE:
<221> NAME/KEY: MISC_FEATURE
<222> LOCATION: (15)..(15)
<223> OTHER INFORMATION: no consensus as to a.a. at time of filing
<220> FEATURE:
<221> NAME/KEY: MISC_FEATURE
<222> LOCATION: (16)..(16)
```

```
<223> OTHER INFORMATION: no consensus as to a.a. at time of filing
<220> FEATURE:
<221> NAME/KEY: MISC_FEATURE
<222> LOCATION: (36)..(36)
<223> OTHER INFORMATION: no consensus as to a.a. at time of filing
<220> FEATURE:
<221> NAME/KEY: MISC_FEATURE
<222> LOCATION: (4)..(4)
<223> OTHER INFORMATION: no consensus as to a.a. at time of filing

<400> SEQUENCE: 9

Arg Ser Leu Xaa Asn Thr Val Ala Thr Leu Tyr Cys Val His Xaa Xaa
1               5                   10                  15

Ile Glu Val Arg Asp Thr Lys Glu Ala Leu Asp Lys Ile Glu Glu Glu
            20                  25                  30

Gln Asn Lys Xaa Gln
        35

<210> SEQ ID NO 10
<211> LENGTH: 37
<212> TYPE: PRT
<213> ORGANISM: Artificial Sequence
<220> FEATURE:
<223> OTHER INFORMATION: Peptide construct
<220> FEATURE:
<221> NAME/KEY: MISC_FEATURE
<222> LOCATION: (4)..(4)
<223> OTHER INFORMATION: no consensus as to the a.a at time of filing

<400> SEQUENCE: 10

Lys Ser Leu Xaa Asn Thr Val Ala Thr Leu Tyr Cys Val His Glu Arg
1               5                   10                  15

Ile Glu Val Lys Asp Thr Lys Glu Ala Leu Glu Lys Met Glu Glu Glu
            20                  25                  30

Gln Asn Lys Ser Lys
        35

<210> SEQ ID NO 11
<211> LENGTH: 37
<212> TYPE: PRT
<213> ORGANISM: Artificial Sequence
<220> FEATURE:
<223> OTHER INFORMATION: Peptide construct

<400> SEQUENCE: 11

Arg Ser Leu Tyr Asn Thr Val Ala Val Leu Tyr Phe Val His Gln Arg
1               5                   10                  15

Val Glu Val Lys Asp Thr Lys Glu Ala Leu Asp Lys Leu Glu Glu Glu
            20                  25                  30

Gln Asn Lys Ser Gln
        35

<210> SEQ ID NO 12
<211> LENGTH: 37
<212> TYPE: PRT
<213> ORGANISM: Artificial Sequence
<220> FEATURE:
<223> OTHER INFORMATION: Peptide construct
<220> FEATURE:
<221> NAME/KEY: MISC_FEATURE
<222> LOCATION: (11)..(11)
<223> OTHER INFORMATION: no consensus as to a.a. at time of filing
<220> FEATURE:
<221> NAME/KEY: MISC_FEATURE
<222> LOCATION: (13)..(13)
<223> OTHER INFORMATION: no consensus as to a.a. at time of filing
<220> FEATURE:
```

```
<221> NAME/KEY: MISC_FEATURE
<222> LOCATION: (4)..(4)
<223> OTHER INFORMATION: no consensus as to a.a. at time of filing
<220> FEATURE:
<221> NAME/KEY: MISC_FEATURE
<222> LOCATION: (6)..(6)
<223> OTHER INFORMATION: no consensus as to a.a. at time of filing
<220> FEATURE:
<221> NAME/KEY: MISC_FEATURE
<222> LOCATION: (7)..(7)
<223> OTHER INFORMATION: no consensus as to a.a. at time of filing
<220> FEATURE:
<221> NAME/KEY: MISC_FEATURE
<222> LOCATION: (9)..(9)
<223> OTHER INFORMATION: no consensus as to a.a. at time of filing

<400> SEQUENCE: 12

Lys Ser Leu Xaa Asn Xaa Xaa Ala Xaa Leu Xaa Cys Xaa His Gln Arg
1               5                   10                  15

Ile Glu Val Lys Asp Thr Lys Glu Ala Leu Glu Glu Val Glu Lys Ala
            20                  25                  30

Gln Lys Asn Ser Gln
        35

<210> SEQ ID NO 13
<211> LENGTH: 37
<212> TYPE: PRT
<213> ORGANISM: Artificial Sequence
<220> FEATURE:
<223> OTHER INFORMATION: Peptide construct
<220> FEATURE:
<221> NAME/KEY: MISC_FEATURE
<222> LOCATION: (19)..(19)
<223> OTHER INFORMATION: no consensus as to a.a. at time of filing
<220> FEATURE:
<221> NAME/KEY: MISC_FEATURE
<222> LOCATION: (27)..(27)
<223> OTHER INFORMATION: no consensus as to a.a. at time of filing
<220> FEATURE:
<221> NAME/KEY: MISC_FEATURE
<222> LOCATION: (29)..(29)
<223> OTHER INFORMATION: no consensus as to a.a. at time of filing
<220> FEATURE:
<221> NAME/KEY: MISC_FEATURE
<222> LOCATION: (30)..(30)
<223> OTHER INFORMATION: no consensus as to a.a. at time of filing
<220> FEATURE:
<221> NAME/KEY: MISC_FEATURE
<222> LOCATION: (32)..(32)
<223> OTHER INFORMATION: no consensus as to a.a. at time of filing
<220> FEATURE:
<221> NAME/KEY: MISC_FEATURE
<222> LOCATION: (35)..(35)
<223> OTHER INFORMATION: no consensus as to a.a. at time of filing
<220> FEATURE:
<221> NAME/KEY: MISC_FEATURE
<222> LOCATION: (36)..(36)
<223> OTHER INFORMATION: no consensus as to a.a. at time of filing
<220> FEATURE:
<221> NAME/KEY: MISC_FEATURE
<222> LOCATION: (9)..(9)
<223> OTHER INFORMATION: no consensus as to a.a. at time of filing

<400> SEQUENCE: 13

Gln Ser Leu Phe Asn Leu Leu Ala Xaa Leu Tyr Cys Val His Gln Arg
1               5                   10                  15

Ile Asp Xaa Lys Asp Thr Lys Glu Ala Leu Xaa Lys Xaa Xaa Glu Xaa
            20                  25                  30

Gln Asn Xaa Xaa Gln
        35
```

```
<210> SEQ ID NO 14
<211> LENGTH: 37
<212> TYPE: PRT
<213> ORGANISM: Artificial Sequence
<220> FEATURE:
<223> OTHER INFORMATION: Peptide construct
<220> FEATURE:
<221> NAME/KEY: MISC_FEATURE
<222> LOCATION: (18)..(18)
<223> OTHER INFORMATION: no consensus as to a.a. at time of filing
<220> FEATURE:
<221> NAME/KEY: MISC_FEATURE
<222> LOCATION: (20)..(20)
<223> OTHER INFORMATION: no consensus as to a.a. at time of filing
<220> FEATURE:
<221> NAME/KEY: MISC_FEATURE
<222> LOCATION: (34)..(34)
<223> OTHER INFORMATION: no consensus as to a.a. at time of filing
<220> FEATURE:
<221> NAME/KEY: MISC_FEATURE
<222> LOCATION: (8)..(8)
<223> OTHER INFORMATION: no consensus as to a.a. at time of filing
<220> FEATURE:
<221> NAME/KEY: MISC_FEATURE
<222> LOCATION: (1)..(1)
<223> OTHER INFORMATION: no consensus as to a.a. at time of filing
<220> FEATURE:
<221> NAME/KEY: MISC_FEATURE
<222> LOCATION: (17)..(17)
<223> OTHER INFORMATION: no consensus as to a.a. at time of filing

<400> SEQUENCE: 14

Xaa Ser Leu Trp Asn Ala Ile Xaa Val Leu Trp Cys Val His Asn Arg
1               5                   10                  15

Xaa Xaa Ile Xaa Asp Thr Gln Gln Ala Ile Gln Lys Leu Lys Glu Val
            20                  25                  30

Met Xaa Ser Arg Lys
        35

<210> SEQ ID NO 15
<211> LENGTH: 28
<212> TYPE: PRT
<213> ORGANISM: Artificial Sequence
<220> FEATURE:
<223> OTHER INFORMATION: Peptide construct

<400> SEQUENCE: 15

Lys Ser Leu Phe Asn Thr Val Ala Val Leu Tyr Cys Val His Gln Arg
1               5                   10                  15

Ile Glu Val Lys Asp Thr Lys Glu Ala Leu Asp Lys
            20                  25

<210> SEQ ID NO 16
<211> LENGTH: 30
<212> TYPE: PRT
<213> ORGANISM: Artificial Sequence
<220> FEATURE:
<223> OTHER INFORMATION: Peptide construct

<400> SEQUENCE: 16

Tyr Cys Val His Gln Lys Ile Glu Val Lys Asp Thr Lys Glu Ala Leu
1               5                   10                  15

Glu Lys Ile Glu Glu Glu Gln Asn Lys Ser Lys Lys Lys Ala
            20                  25                  30

<210> SEQ ID NO 17
<211> LENGTH: 30
<212> TYPE: PRT
<213> ORGANISM: Artificial Sequence
```

```
<220> FEATURE:
<223> OTHER INFORMATION: Peptide construct

<400> SEQUENCE: 17

Trp Cys Val His Gln Arg Ile Glu Val Lys Asp Thr Lys Glu Ala Leu
1               5                   10                  15

Asp Lys Ile Glu Glu Val Gln Asn Lys Ser Gln Gln Lys Thr
            20                  25                  30

<210> SEQ ID NO 18
<211> LENGTH: 30
<212> TYPE: PRT
<213> ORGANISM: Artificial Sequence
<220> FEATURE:
<223> OTHER INFORMATION: Peptide construct

<400> SEQUENCE: 18

Tyr Cys Val His Gln Arg Ile Asp Val Lys Asp Thr Lys Glu Ala Leu
1               5                   10                  15

Asn Lys Ile Glu Glu Met Gln Asn Lys Asn Lys Gln Arg Thr
            20                  25                  30

<210> SEQ ID NO 19
<211> LENGTH: 30
<212> TYPE: PRT
<213> ORGANISM: Artificial Sequence
<220> FEATURE:
<223> OTHER INFORMATION: Peptide construct

<400> SEQUENCE: 19

Tyr Cys Val His Gln Arg Ile Asp Val Lys Asp Thr Lys Glu Ala Leu
1               5                   10                  15

Asp Lys Ile Glu Glu Ile Gln Asn Lys Ser Lys Gln Lys Thr
            20                  25                  30

<210> SEQ ID NO 20
<211> LENGTH: 30
<212> TYPE: PRT
<213> ORGANISM: Artificial Sequence
<220> FEATURE:
<223> OTHER INFORMATION: Peptide construct

<400> SEQUENCE: 20

Tyr Phe Val His Gln Arg Val Glu Val Lys Asp Thr Lys Glu Ala Leu
1               5                   10                  15

Asp Lys Leu Glu Glu Glu Gln Asn Lys Ser Gln Gln Lys Thr
            20                  25                  30

<210> SEQ ID NO 21
<211> LENGTH: 30
<212> TYPE: PRT
<213> ORGANISM: Artificial Sequence
<220> FEATURE:
<223> OTHER INFORMATION: Peptide construct

<400> SEQUENCE: 21

Tyr Cys Val His Gln Lys Ile Asp Val Arg Asp Thr Lys Glu Ala Leu
1               5                   10                  15

Glu Lys Val Glu Glu Glu Gln Asn Lys Ser Lys Glu Lys Ala
            20                  25                  30

<210> SEQ ID NO 22
<211> LENGTH: 30
<212> TYPE: PRT
```

<213> ORGANISM: Artificial Sequence
<220> FEATURE:
<223> OTHER INFORMATION: Peptide construct

<400> SEQUENCE: 22

Tyr Cys Val His Gln Arg Ile Asp Val Lys Asp Thr Lys Glu Ala Leu
1               5                   10                  15

Asp Lys Ile Glu Glu Glu Gln Asn Lys Ser Lys Lys Lys Glu
            20                  25                  30

<210> SEQ ID NO 23
<211> LENGTH: 30
<212> TYPE: PRT
<213> ORGANISM: Artificial Sequence
<220> FEATURE:
<223> OTHER INFORMATION: Peptide construct

<400> SEQUENCE: 23

Tyr Cys Val His Lys Gly Ile Glu Val Arg Asp Thr Lys Glu Ala Leu
1               5                   10                  15

Asp Lys Ile Glu Glu Glu Gln Asn Lys Ile Gln Gln Lys Thr
            20                  25                  30

<210> SEQ ID NO 24
<211> LENGTH: 30
<212> TYPE: PRT
<213> ORGANISM: Artificial Sequence
<220> FEATURE:
<223> OTHER INFORMATION: Peptide construct
<220> FEATURE:
<221> NAME/KEY: MISC_FEATURE
<222> LOCATION: (26)..(26)
<223> OTHER INFORMATION: no consensus as to a.a. at time of filing
<220> FEATURE:
<221> NAME/KEY: MISC_FEATURE
<222> LOCATION: (5)..(5)
<223> OTHER INFORMATION: no consensus as to a.a. at time of filing
<220> FEATURE:
<221> NAME/KEY: MISC_FEATURE
<222> LOCATION: (6)..(6)
<223> OTHER INFORMATION: no consensus as to a.a. at time of filing

<400> SEQUENCE: 24

Tyr Cys Val His Xaa Xaa Ile Glu Val Arg Asp Thr Lys Glu Ala Leu
1               5                   10                  15

Asp Lys Ile Glu Glu Glu Gln Asn Lys Xaa Gln Gln Lys Thr
            20                  25                  30

<210> SEQ ID NO 25
<211> LENGTH: 30
<212> TYPE: PRT
<213> ORGANISM: Artificial Sequence
<220> FEATURE:
<223> OTHER INFORMATION: Peptide construct

<400> SEQUENCE: 25

Tyr Cys Val His Glu Arg Ile Lys Val Ala Asp Thr Lys Glu Ala Leu
1               5                   10                  15

Asp Lys Ile Glu Glu Glu Gln Thr Lys Ser Lys Lys Lys Ala
            20                  25                  30

<210> SEQ ID NO 26
<211> LENGTH: 37
<212> TYPE: PRT
<213> ORGANISM: Artificial Sequence
<220> FEATURE:
<223> OTHER INFORMATION: Peptide construct

```
<400> SEQUENCE: 26

Arg Ser Leu Tyr Asn Thr Val Ala Thr Leu Tyr Cys Val His Gln Arg
1               5                   10                  15

Ile Asp Val Lys Asp Thr Lys Glu Ala Leu Glu Lys Ile Glu Glu Glu
            20                  25                  30

Lys Gln Lys Ser Lys
        35

<210> SEQ ID NO 27
<211> LENGTH: 37
<212> TYPE: PRT
<213> ORGANISM: Artificial Sequence
<220> FEATURE:
<223> OTHER INFORMATION: Peptide construct

<400> SEQUENCE: 27

Lys Ser Leu Tyr Asn Thr Val Ala Thr Leu Tyr Cys Val His Gln Lys
1               5                   10                  15

Ile Glu Ile Lys Asp Thr Lys Glu Ala Leu Glu Lys Ile Glu Glu Glu
            20                  25                  30

Gln Asn Lys Ser Lys
        35

<210> SEQ ID NO 28
<211> LENGTH: 6
<212> TYPE: PRT
<213> ORGANISM: Artificial Sequence
<220> FEATURE:
<223> OTHER INFORMATION: Peptide construct

<400> SEQUENCE: 28

Gly Gly Gly Gly Ser Ser
1               5

<210> SEQ ID NO 29
<211> LENGTH: 12
<212> TYPE: PRT
<213> ORGANISM: Artificial Sequence
<220> FEATURE:
<223> OTHER INFORMATION: Peptide construct

<400> SEQUENCE: 29

Gly Gly Gly Gly Ser Gly Gly Gly Ser Gly Gly
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Peptide construct

<400> SEQUENCE: 30

Gly Gly Gly Ser Gly Thr Gly Ser Gly Ser Gly Ser
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Peptide construct

<400> SEQUENCE: 31
```

```
Gly Gly Gly Gly Ser Gly Gly Gly Ser Gly Gly Gly Ser
1               5                  10

<210> SEQ ID NO 32
<211> LENGTH: 7
<212> TYPE: PRT
<213> ORGANISM: Artificial Sequence
<220> FEATURE:
<223> OTHER INFORMATION: Peptide construct

<400> SEQUENCE: 32

Lys Gly Lys Gly Lys Gly Leu
1               5

<210> SEQ ID NO 33
<211> LENGTH: 19
<212> TYPE: PRT
<213> ORGANISM: Artificial Sequence
<220> FEATURE:
<223> OTHER INFORMATION: Peptide construct

<400> SEQUENCE: 33

Val Ala Lys Leu Glu Ala Lys Val Ala Lys Leu Glu Ala Lys Gly Lys
1               5                   10                  15

Gly Lys Tyr

<210> SEQ ID NO 34
<211> LENGTH: 13
<212> TYPE: PRT
<213> ORGANISM: Artificial Sequence
<220> FEATURE:
<223> OTHER INFORMATION: Peptide J from a region of Beta-2 microglobulin
      (38-50)

<400> SEQUENCE: 34

Asp Leu Leu Lys Asn Gly Glu Arg Ile Glu Lys Val Glu
1               5                   10

<210> SEQ ID NO 35
<211> LENGTH: 9
<212> TYPE: PRT
<213> ORGANISM: Artificial Sequence
<220> FEATURE:
<223> OTHER INFORMATION: Peptide F from a region IL-1Beta (163-171)

<400> SEQUENCE: 35

Val Gln Gly Glu Glu Ser Asn Asp Lys
1               5

<210> SEQ ID NO 36
<211> LENGTH: 30
<212> TYPE: PRT
<213> ORGANISM: Artificial Sequence
<220> FEATURE:
<223> OTHER INFORMATION: fragment of HIV p17gag HGP30

<400> SEQUENCE: 36

Tyr Ser Val His Gln Arg Ile Asp Val Lys Asp Thr Lys Glu Ala Leu
1               5                   10                  15

Glu Lys Ile Glu Glu Glu Gln Asn Lys Ser Lys Lys Lys Ala
            20                  25                  30

<210> SEQ ID NO 37
<211> LENGTH: 47
<212> TYPE: PRT
```

```
<213> ORGANISM: Artificial Sequence
<220> FEATURE:
<223> OTHER INFORMATION: Peptide construct

<400> SEQUENCE: 37

Asp Gly Gln Glu Glu Lys Ala Gly Val Val Ser Thr Gly Leu Ile Gly
 1               5                  10                  15

Gly Gly Ala Thr Leu Tyr Ser Val His Gln Arg Ile Asp Val Lys Asp
                20                  25                  30

Thr Lys Glu Ala Leu Glu Lys Ile Glu Glu Glu Gln Asn Lys Ser
         35                  40                  45

<210> SEQ ID NO 38
<211> LENGTH: 47
<212> TYPE: PRT
<213> ORGANISM: Artificial Sequence
<220> FEATURE:
<223> OTHER INFORMATION: Peptide construct

<400> SEQUENCE: 38

Asn Gly Gln Glu Glu Lys Ala Gly Val Val Ser Thr Gly Leu Ile Gly
 1               5                  10                  15

Gly Gly Ala Thr Leu Tyr Ser Val His Gln Arg Ile Asp Val Lys Asp
                20                  25                  30

Thr Lys Glu Ala Leu Glu Lys Ile Glu Glu Glu Gln Asn Lys Ser
         35                  40                  45

<210> SEQ ID NO 39
<211> LENGTH: 45
<212> TYPE: PRT
<213> ORGANISM: Artificial Sequence
<220> FEATURE:
<223> OTHER INFORMATION: Peptide construct

<400> SEQUENCE: 39

Asp Leu Leu Lys Asn Gly Glu Arg Ile Glu Lys Val Glu Gly Gly Gly
 1               5                  10                  15

Ala Thr Leu Tyr Ser Val His Gln Arg Ile Asp Val Lys Asp Thr Lys
                20                  25                  30

Glu Ala Leu Glu Lys Ile Glu Glu Glu Gln Asn Lys Ser
         35                  40                  45

<210> SEQ ID NO 40
<211> LENGTH: 41
<212> TYPE: PRT
<213> ORGANISM: Artificial Sequence
<220> FEATURE:
<223> OTHER INFORMATION: Peptide construct

<400> SEQUENCE: 40

Val Gln Gly Glu Glu Ser Asn Asp Lys Gly Gly Gly Ala Thr Leu Tyr
 1               5                  10                  15

Ser Val His Gln Arg Ile Cys Val Lys Asp Thr Lys Glu Ala Leu Glu
                20                  25                  30

Lys Ile Glu Glu Glu Gln Asn Lys Ser
         35                  40

<210> SEQ ID NO 41
<211> LENGTH: 42
<212> TYPE: PRT
<213> ORGANISM: Artificial Sequence
<220> FEATURE:
<223> OTHER INFORMATION: Peptide construct
```

```
<400> SEQUENCE: 41

Val Gln Gly Glu Glu Ser Asn Asp Lys Gly Gly Tyr Ser Val His
1               5                   10                  15

Gln Arg Ile Asp Val Lys Asp Thr Lys Glu Ala Leu Glu Lys Ile Glu
            20                  25                  30

Glu Glu Gln Asn Lys Ser Lys Lys Ala
        35                  40

<210> SEQ ID NO 42
<211> LENGTH: 19
<212> TYPE: PRT
<213> ORGANISM: Artificial Sequence
<220> FEATURE:
<223> OTHER INFORMATION: Peptide My

<400> SEQUENCE: 42

Asp Ser Ala Phe Asp Val Leu Ser Phe Thr Ala Glu Glu Lys Ala Gly
1               5                   10                  15

Val Tyr Lys

<210> SEQ ID NO 43
<211> LENGTH: 8
<212> TYPE: PRT
<213> ORGANISM: Artificial Sequence
<220> FEATURE:
<223> OTHER INFORMATION: Muc1 Peptide M1a

<400> SEQUENCE: 43

Ala Pro Asp Thr Arg Pro Ala Pro
1               5

<210> SEQ ID NO 44
<211> LENGTH: 9
<212> TYPE: PRT
<213> ORGANISM: Artificial Sequence
<220> FEATURE:
<223> OTHER INFORMATION: Muc1 Peptide M1b

<400> SEQUENCE: 44

Ser Thr Ala Pro Pro Ala His Gly Val
1               5

<210> SEQ ID NO 45
<211> LENGTH: 20
<212> TYPE: PRT
<213> ORGANISM: Artificial Sequence
<220> FEATURE:
<223> OTHER INFORMATION: Muc1 Peptide M1c

<400> SEQUENCE: 45

Gly Val Thr Ser Ala Pro Asp Thr Arg Pro Ala Pro Gly Ser Thr Ala
1               5                   10                  15

Pro Pro Ala His
            20

<210> SEQ ID NO 46
<211> LENGTH: 9
<212> TYPE: PRT
<213> ORGANISM: Artificial Sequence
<220> FEATURE:
<223> OTHER INFORMATION: CEA Peptide C1

<400> SEQUENCE: 46
```

-continued

```
Tyr Ser Leu Gly Ala Asn Leu Asn Leu
1               5

<210> SEQ ID NO 47
<211> LENGTH: 8
<212> TYPE: PRT
<213> ORGANISM: Artificial Sequence
<220> FEATURE:
<223> OTHER INFORMATION: CEA Peptide C2

<400> SEQUENCE: 47

Glu Ala Gln Asn Thr Thr Tyr Leu
1               5

<210> SEQ ID NO 48
<211> LENGTH: 10
<212> TYPE: PRT
<213> ORGANISM: Artificial Sequence
<220> FEATURE:
<223> OTHER INFORMATION: CEA Peptide C3

<400> SEQUENCE: 48

Gln Tyr Ser Trp Phe Val Asn Gly Thr Phe
1               5                   10

<210> SEQ ID NO 49
<211> LENGTH: 9
<212> TYPE: PRT
<213> ORGANISM: Artificial Sequence
<220> FEATURE:
<223> OTHER INFORMATION: CEA Peptide C4

<400> SEQUENCE: 49

Thr Tyr Ala Cys Phe Val Ser Asn Leu
1               5

<210> SEQ ID NO 50
<211> LENGTH: 9
<212> TYPE: PRT
<213> ORGANISM: Artificial Sequence
<220> FEATURE:
<223> OTHER INFORMATION: CEA Peptide C5

<400> SEQUENCE: 50

Ile Tyr Pro Asn Ala Ser Leu Leu Ile
1               5

<210> SEQ ID NO 51
<211> LENGTH: 16
<212> TYPE: PRT
<213> ORGANISM: Artificial Sequence
<220> FEATURE:
<223> OTHER INFORMATION: Herpes Simplex Virus gD1 (8-23)

<400> SEQUENCE: 51

Ser Leu Lys Met Ala Asp Pro Asn Arg Phe Arg Gly Lys Asp Leu Pro
1               5                   10                  15

<210> SEQ ID NO 52
<211> LENGTH: 23
<212> TYPE: PRT
<213> ORGANISM: Artificial Sequence
<220> FEATURE:
<223> OTHER INFORMATION: Herpes Simplex Virus gD1 (1-23)

<400> SEQUENCE: 52

Lys Tyr Ala Leu Ala Asp Ala Ser Leu Lys Met Ala Asp Pro Asn Arg
```

```
                1               5                  10                 15
Phe Arg Gly Lys Asp Leu Pro
                20

<210> SEQ ID NO 53
<211> LENGTH: 22
<212> TYPE: PRT
<213> ORGANISM: Artificial Sequence
<220> FEATURE:
<223> OTHER INFORMATION: Herpes Simplex Virus extg B1

<400> SEQUENCE: 53

Glu Arg Ile Lys Thr Thr Ser Ser Ile Glu Phe Ala Arg Leu Gln Phe
1               5                  10                 15

Thr Thr Asp His Ile Gln
                20

<210> SEQ ID NO 54
<211> LENGTH: 26
<212> TYPE: PRT
<213> ORGANISM: Artificial Sequence
<220> FEATURE:
<223> OTHER INFORMATION: Peptide construct

<400> SEQUENCE: 54

Asp Gly Gln Glu Glu Lys Ala Gly Val Val Ser Thr Gly Leu Ile Gly
1               5                  10                 15

Gly Gly Ala Pro Asp Thr Arg Pro Ala Pro
                20                  25

<210> SEQ ID NO 55
<211> LENGTH: 27
<212> TYPE: PRT
<213> ORGANISM: Artificial Sequence
<220> FEATURE:
<223> OTHER INFORMATION: Peptide construct

<400> SEQUENCE: 55

Asp Gly Gln Glu Glu Lys Ala Gly Val Val Ser Thr Gly Leu Ile Gly
1               5                  10                 15

Gly Gly Ser Thr Ala Pro Pro Ala His Gly Val
                20                  25

<210> SEQ ID NO 56
<211> LENGTH: 38
<212> TYPE: PRT
<213> ORGANISM: Artificial Sequence
<220> FEATURE:
<223> OTHER INFORMATION: Peptide construct

<400> SEQUENCE: 56

Asp Gly Gln Glu Glu Lys Ala Gly Val Val Ser Thr Gly Leu Ile Gly
1               5                  10                 15

Gly Gly Gly Val Thr Ser Ala Pro Asp Thr Arg Pro Ala Pro Gly Ser
                20                  25                  30

Thr Ala Pro Pro Ala His
                35

<210> SEQ ID NO 57
<211> LENGTH: 27
<212> TYPE: PRT
<213> ORGANISM: Artificial Sequence
<220> FEATURE:
<223> OTHER INFORMATION: Peptide construct
```

```
<400> SEQUENCE: 57

Asp Gly Gln Glu Glu Lys Ala Gly Val Val Ser Thr Gly Leu Ile Gly
1               5                   10                  15

Gly Gly Tyr Leu Ser Gly Ala Asn Leu Asn Leu
            20                  25

<210> SEQ ID NO 58
<211> LENGTH: 26
<212> TYPE: PRT
<213> ORGANISM: Artificial Sequence
<220> FEATURE:
<223> OTHER INFORMATION: Peptide construct

<400> SEQUENCE: 58

Asp Gly Gln Glu Glu Lys Ala Gly Val Val Ser Thr Gly Leu Ile Gly
1               5                   10                  15

Gly Gly Glu Ala Gln Asn Thr Thr Tyr Leu
            20                  25

<210> SEQ ID NO 59
<211> LENGTH: 28
<212> TYPE: PRT
<213> ORGANISM: Artificial Sequence
<220> FEATURE:
<223> OTHER INFORMATION: Peptide construct

<400> SEQUENCE: 59

Asp Gly Gln Glu Glu Lys Ala Gly Val Val Ser Thr Gly Leu Ile Gly
1               5                   10                  15

Gly Gly Gln Tyr Ser Trp Phe Val Asn Gly Thr Phe
            20                  25

<210> SEQ ID NO 60
<211> LENGTH: 27
<212> TYPE: PRT
<213> ORGANISM: Artificial Sequence
<220> FEATURE:
<223> OTHER INFORMATION: Peptide construct

<400> SEQUENCE: 60

Asp Gly Gln Glu Glu Lys Ala Gly Val Val Ser Thr Gly Leu Ile Gly
1               5                   10                  15

Gly Gly Thr Tyr Ala Cys Phe Val Ser Asn Leu
            20                  25

<210> SEQ ID NO 61
<211> LENGTH: 27
<212> TYPE: PRT
<213> ORGANISM: Artificial Sequence
<220> FEATURE:
<223> OTHER INFORMATION: Peptide construct

<400> SEQUENCE: 61

Asp Gly Gln Glu Glu Lys Ala Gly Val Val Ser Thr Gly Leu Ile Gly
1               5                   10                  15

Gly Gly Ile Tyr Pro Asn Ala Ser Leu Leu Ile
            20                  25

<210> SEQ ID NO 62
<211> LENGTH: 24
<212> TYPE: PRT
<213> ORGANISM: Artificial Sequence
<220> FEATURE:
```

<223> OTHER INFORMATION: Peptide construct

<400> SEQUENCE: 62

Asp Leu Leu Lys Asn Gly Glu Arg Ile Glu Lys Val Glu Gly Gly Gly
1               5                   10                  15
Ala Pro Asp Thr Arg Pro Ala Pro
            20

<210> SEQ ID NO 63
<211> LENGTH: 25
<212> TYPE: PRT
<213> ORGANISM: Artificial Sequence
<220> FEATURE:
<223> OTHER INFORMATION: Peptide construct

<400> SEQUENCE: 63

Asp Leu Leu Lys Asn Gly Glu Arg Ile Glu Lys Val Glu Gly Gly Gly
1               5                   10                  15
Ser Thr Ala Pro Pro Ala His Gly Val
            20                  25

<210> SEQ ID NO 64
<211> LENGTH: 36
<212> TYPE: PRT
<213> ORGANISM: Artificial Sequence
<220> FEATURE:
<223> OTHER INFORMATION: Peptide construct

<400> SEQUENCE: 64

Asp Leu Leu Lys Asn Gly Glu Arg Ile Glu Lys Val Glu Gly Gly Gly
1               5                   10                  15
Gly Val Thr Ser Ala Pro Asp Thr Arg Pro Ala Pro Gly Ser Thr Ala
            20                  25                  30
Pro Pro Ala His
        35

<210> SEQ ID NO 65
<211> LENGTH: 25
<212> TYPE: PRT
<213> ORGANISM: Artificial Sequence
<220> FEATURE:
<223> OTHER INFORMATION: Peptide construct

<400> SEQUENCE: 65

Asp Leu Leu Lys Asn Gly Glu Arg Ile Glu Lys Val Glu Gly Gly Gly
1               5                   10                  15
Tyr Leu Ser Gly Ala Asn Leu Asn Leu
            20                  25

<210> SEQ ID NO 66
<211> LENGTH: 24
<212> TYPE: PRT
<213> ORGANISM: Artificial Sequence
<220> FEATURE:
<223> OTHER INFORMATION: Peptide construct

<400> SEQUENCE: 66

Asp Leu Leu Lys Asn Gly Glu Arg Ile Glu Lys Val Glu Gly Gly Gly
1               5                   10                  15
Glu Ala Gln Asn Thr Thr Tyr Leu
            20

<210> SEQ ID NO 67

```
<211> LENGTH: 26
<212> TYPE: PRT
<213> ORGANISM: Artificial Sequence
<220> FEATURE:
<223> OTHER INFORMATION: Peptide construct

<400> SEQUENCE: 67

Asp Leu Leu Lys Asn Gly Glu Arg Ile Glu Lys Val Glu Gly Gly Gly
1               5                   10                  15

Gln Tyr Ser Trp Val Val Asn Gly Thr Phe
            20                  25

<210> SEQ ID NO 68
<211> LENGTH: 25
<212> TYPE: PRT
<213> ORGANISM: Artificial Sequence
<220> FEATURE:
<223> OTHER INFORMATION: Peptide construct

<400> SEQUENCE: 68

Asp Leu Leu Lys Asn Gly Glu Arg Ile Glu Lys Val Glu Gly Gly Gly
1               5                   10                  15

Thr Tyr Ala Cys Phe Val Ser Asn Leu
            20                  25

<210> SEQ ID NO 69
<211> LENGTH: 25
<212> TYPE: PRT
<213> ORGANISM: Artificial Sequence
<220> FEATURE:
<223> OTHER INFORMATION: Peptide construct

<400> SEQUENCE: 69

Asp Leu Leu Lys Asn Gly Glu Arg Ile Glu Lys Val Glu Gly Gly Gly
1               5                   10                  15

Ile Tyr Pro Asn Ala Ser Leu Leu Ile
            20                  25

<210> SEQ ID NO 70
<211> LENGTH: 41
<212> TYPE: PRT
<213> ORGANISM: Artificial Sequence
<220> FEATURE:
<223> OTHER INFORMATION: Peptide construct

<400> SEQUENCE: 70

Asp Gly Gln Glu Glu Lys Ala Gly Val Val Ser Thr Gly Leu Ile Gly
1               5                   10                  15

Gly Gly Lys Tyr Ala Leu Ala Asp Ala Ser Leu Lys Met Ala Asp Pro
            20                  25                  30

Asn Arg Phe Arg Gly Lys Asp Leu Pro
        35                  40

<210> SEQ ID NO 71
<211> LENGTH: 38
<212> TYPE: PRT
<213> ORGANISM: Artificial Sequence
<220> FEATURE:
<223> OTHER INFORMATION: Peptide construct

<400> SEQUENCE: 71

Asp Leu Leu Lys Asn Gly Glu Arg Ile Glu Lys Val Glu Gly Gly Gly
1               5                   10                  15

Lys Tyr Leu Ala Asp Ala Ser Leu Lys Met Ala Asp Pro Asn Arg Phe
```

-continued

```
                 20                  25                  30

Arg Gly Lys Asp Leu Pro
        35

<210> SEQ ID NO 72
<211> LENGTH: 34
<212> TYPE: PRT
<213> ORGANISM: Artificial Sequence
<220> FEATURE:
<223> OTHER INFORMATION: Peptide construct

<400> SEQUENCE: 72

Asp Gly Gln Glu Glu Lys Ala Gly Val Val Ser Thr Gly Leu Ile Gly
1               5                   10                  15

Gly Gly Ser Leu Lys Met Ala Asp Pro Asn Arg Phe Arg Gly Lys Asp
            20                  25                  30

Leu Pro

<210> SEQ ID NO 73
<211> LENGTH: 32
<212> TYPE: PRT
<213> ORGANISM: Artificial Sequence
<220> FEATURE:
<223> OTHER INFORMATION: Peptide construct

<400> SEQUENCE: 73

Asp Leu Leu Lys Asn Gly Glu Arg Ile Glu Lys Val Glu Gly Gly Gly
1               5                   10                  15

Ser Leu Lys Met Ala Asp Pro Asn Arg Phe Arg Gly Lys Asp Leu Pro
            20                  25                  30

<210> SEQ ID NO 74
<211> LENGTH: 53
<212> TYPE: PRT
<213> ORGANISM: Artificial Sequence
<220> FEATURE:
<223> OTHER INFORMATION: Peptide construct

<400> SEQUENCE: 74

Asp Leu Leu Lys Asn Gly Glu Arg Ile Glu Lys Val Glu Gly Gly Gly
1               5                   10                  15

Leu Tyr Arg Thr Phe Ala Gly Asn Pro Arg Ala Gly Gly Gly Lys Tyr
            20                  25                  30

Ala Leu Ala Asp Ala Ser Leu Lys Met Ala Asp Pro Asn Arg Phe Arg
        35                  40                  45

Gly Lys Asp Leu Pro
    50

<210> SEQ ID NO 75
<211> LENGTH: 38
<212> TYPE: PRT
<213> ORGANISM: Artificial Sequence
<220> FEATURE:
<223> OTHER INFORMATION: Peptide construct

<400> SEQUENCE: 75

Asp Leu Leu Lys Asn Gly Glu Arg Ile Glu Gly Val Glu Gly Gly Gly
1               5                   10                  15

Glu Arg Ile Lys Thr Thr Ser Ser Ile Glu Phe Ala Arg Leu Gln Phe
            20                  25                  30

Thr Thr Asp His Ile Gln
        35
```

<210> SEQ ID NO 76
<211> LENGTH: 40
<212> TYPE: PRT
<213> ORGANISM: Artificial Sequence
<220> FEATURE:
<223> OTHER INFORMATION: Peptide construct

<400> SEQUENCE: 76

Asp Gly Gln Glu Glu Lys Ala Gly Val Val Ser Thr Gly Leu Ile Gly
1               5                   10                  15

Gly Gly Glu Arg Ile Lys Thr Thr Ser Ser Ile Glu Phe Ala Arg Leu
            20                  25                  30

Gln Phe Thr Thr Asp His Ile Gln
        35                  40

<210> SEQ ID NO 77
<211> LENGTH: 44
<212> TYPE: PRT
<213> ORGANISM: Artificial Sequence
<220> FEATURE:
<223> OTHER INFORMATION: Peptide construct

<400> SEQUENCE: 77

Asp Leu Leu Lys Asn Gly Glu Arg Ile Glu Lys Val Glu Gly Gly Gly
1               5                   10                  15

Ala Thr Leu Tyr Ser Val His Gln Arg Ile Asp Val Lys Asp Thr Lys
            20                  25                  30

Glu Ala Leu Glu Lys Ile Glu Glu Gln Asn Lys Ser
        35                  40

<210> SEQ ID NO 78
<211> LENGTH: 49
<212> TYPE: PRT
<213> ORGANISM: Artificial Sequence
<220> FEATURE:
<223> OTHER INFORMATION: Peptide construct

<400> SEQUENCE: 78

Asp Leu Leu Lys Asn Gly Glu Arg Ile Glu Lys Val Glu Gly Gly Gly
1               5                   10                  15

Ser Gly Gly Gly Ala Thr Leu Tyr Ser Val His Gln Arg Ile Asp Val
            20                  25                  30

Lys Asp Thr Lys Glu Ala Leu Glu Lys Ile Glu Glu Gln Asn Lys
        35                  40                  45

Ser

<210> SEQ ID NO 79
<211> LENGTH: 57
<212> TYPE: PRT
<213> ORGANISM: Artificial Sequence
<220> FEATURE:
<223> OTHER INFORMATION: Peptide construct

<400> SEQUENCE: 79

Asp Leu Leu Lys Asn Gly Glu Arg Ile Glu Lys Val Glu Gly Gly Gly
1               5                   10                  15

Gly Ser Gly Gly Gly Gly Ser Gly Gly Gly Ser Ala Thr Leu Tyr
            20                  25                  30

Ser Val His Gln Arg Ile Asp Val Lys Asp Thr Lys Glu Ala Leu Glu
        35                  40                  45

Lys Ile Glu Glu Glu Gln Asn Lys Ser
        50                  55

<210> SEQ ID NO 80
<211> LENGTH: 48
<212> TYPE: PRT
<213> ORGANISM: Artificial Sequence
<220> FEATURE:
<223> OTHER INFORMATION: Peptide construct

<400> SEQUENCE: 80

Asp Leu Leu Lys Asn Gly Glu Arg Ile Glu Lys Val Glu Gly Gly
1               5                   10                  15

Gly Ser Ser Ala Thr Leu Tyr Ser Val His Gln Arg Ile Asp Val Lys
                20                  25                  30

Asp Thr Lys Glu Ala Leu Glu Lys Ile Glu Glu Glu Gln Asn Lys Ser
            35                  40                  45

<210> SEQ ID NO 81
<211> LENGTH: 47
<212> TYPE: PRT
<213> ORGANISM: Artificial Sequence
<220> FEATURE:
<223> OTHER INFORMATION: Peptide construct

<400> SEQUENCE: 81

Asp Gly Gln Glu Glu Lys Ala Gly Val Val Ser Thr Gly Leu Ile Gly
1               5                   10                  15

Gly Gly Ala Thr Leu Tyr Ser Val His Gln Arg Ile Asp Val Lys Asp
                20                  25                  30

Thr Lys Glu Ala Leu Glu Lys Ile Glu Glu Glu Gln Asn Lys Ser
            35                  40                  45

<210> SEQ ID NO 82
<211> LENGTH: 52
<212> TYPE: PRT
<213> ORGANISM: Artificial Sequence
<220> FEATURE:
<223> OTHER INFORMATION: Peptide construct

<400> SEQUENCE: 82

Asp Gly Gln Glu Glu Lys Ala Gly Val Val Ser Thr Gly Leu Ile Gly
1               5                   10                  15

Gly Gly Ser Gly Gly Gly Ser Ala Thr Leu Tyr Ser Val His Gln Arg
                20                  25                  30

Ile Asp Val Lys Asp Thr Lys Glu Ala Leu Glu Lys Ile Glu Glu Glu
            35                  40                  45

Gln Asn Lys Ser
    50

<210> SEQ ID NO 83
<211> LENGTH: 59
<212> TYPE: PRT
<213> ORGANISM: Artificial Sequence
<220> FEATURE:
<223> OTHER INFORMATION: Peptide construct

<400> SEQUENCE: 83

Asp Gly Gln Glu Glu Lys Ala Gly Val Val Ser Thr Gly Leu Ile Gly
1               5                   10                  15

Gly Gly Gly Ser Gly Gly Gly Gly Ser Gly Gly Gly Ser Ala Thr
                20                  25                  30

```
Leu Tyr Ser Val His Gln Arg Ile Asp Val Lys Asp Thr Lys Glu Ala
        35                  40                  45

Leu Glu Lys Ile Glu Glu Gln Asn Lys Ser
    50                  55

<210> SEQ ID NO 84
<211> LENGTH: 50
<212> TYPE: PRT
<213> ORGANISM: Artificial Sequence
<220> FEATURE:
<223> OTHER INFORMATION: Peptide construct

<400> SEQUENCE: 84

Asp Gly Gln Glu Glu Lys Ala Gly Val Val Ser Thr Gly Leu Ile Gly
1               5                   10                  15

Gly Gly Gly Ser Ser Ala Thr Leu Tyr Ser Val His Gln Arg Ile Asp
            20                  25                  30

Val Lys Asp Thr Lys Glu Ala Leu Glu Lys Ile Glu Glu Gln Asn
        35                  40                  45

Lys Ser
    50

<210> SEQ ID NO 85
<211> LENGTH: 51
<212> TYPE: PRT
<213> ORGANISM: Artificial Sequence
<220> FEATURE:
<223> OTHER INFORMATION: Peptide construct

<400> SEQUENCE: 85

Asp Leu Leu Lys Asn Gly Glu Arg Ile Glu Lys Val Glu Gly Gly Gly
1               5                   10                  15

Ser Leu Tyr Asn Thr Val Ala Thr Leu Tyr Ser Val His Gln Arg Ile
            20                  25                  30

Asp Val Lys Asp Thr Lys Glu Ala Leu Glu Lys Ile Glu Glu Gln
        35                  40                  45

Asn Lys Ser
    50

<210> SEQ ID NO 86
<211> LENGTH: 56
<212> TYPE: PRT
<213> ORGANISM: Artificial Sequence
<220> FEATURE:
<223> OTHER INFORMATION: Peptide construct

<400> SEQUENCE: 86

Asp Leu Leu Lys Asn Gly Glu Arg Ile Glu Lys Val Glu Gly Gly Gly
1               5                   10                  15

Ser Gly Gly Ser Ser Leu Tyr Asn Thr Val Ala Thr Leu Tyr Ser
            20                  25                  30

Val His Gln Arg Ile Asp Val Lys Asp Thr Lys Glu Ala Leu Glu Lys
        35                  40                  45

Ile Glu Glu Gln Asn Lys Ser
    50                  55

<210> SEQ ID NO 87
<211> LENGTH: 63
<212> TYPE: PRT
<213> ORGANISM: Artificial Sequence
<220> FEATURE:
<223> OTHER INFORMATION: Peptide construct
```

```
<400> SEQUENCE: 87

Asp Leu Leu Lys Asn Gly Glu Arg Ile Glu Lys Val Glu Gly Gly Gly
1               5                   10                  15

Gly Ser Gly Gly Gly Ser Gly Gly Gly Ser Ser Leu Tyr Asn
            20                  25                  30

Thr Val Ala Thr Leu Tyr Ser Val His Gln Arg Ile Asp Val Lys Asp
            35                  40                  45

Thr Lys Glu Ala Leu Glu Lys Ile Glu Glu Glu Gln Asn Lys Ser
        50                  55                  60

<210> SEQ ID NO 88
<211> LENGTH: 54
<212> TYPE: PRT
<213> ORGANISM: Artificial Sequence
<220> FEATURE:
<223> OTHER INFORMATION: Peptide construct

<400> SEQUENCE: 88

Asp Leu Leu Lys Asn Gly Glu Arg Ile Glu Lys Val Glu Gly Gly Gly
1               5                   10                  15

Gly Ser Ser Ser Leu Tyr Asn Thr Val Ala Thr Leu Tyr Ser Val His
            20                  25                  30

Gln Arg Ile Asp Val Lys Asp Thr Lys Glu Ala Leu Glu Lys Ile Glu
            35                  40                  45

Glu Glu Gln Asn Lys Ser
        50

<210> SEQ ID NO 89
<211> LENGTH: 53
<212> TYPE: PRT
<213> ORGANISM: Artificial Sequence
<220> FEATURE:
<223> OTHER INFORMATION: Peptide construct

<400> SEQUENCE: 89

Asp Gly Gln Glu Glu Lys Ala Gly Val Val Ser Thr Gly Leu Ile Gly
1               5                   10                  15

Gly Gly Ser Leu Tyr Asn Thr Val Ala Thr Leu Tyr Ser Val His Gln
            20                  25                  30

Arg Ile Asp Val Lys Asp Thr Lys Glu Ala Leu Ala Lys Ile Glu Glu
            35                  40                  45

Glu Gln Asn Lys Ser
        50

<210> SEQ ID NO 90
<211> LENGTH: 58
<212> TYPE: PRT
<213> ORGANISM: Artificial Sequence
<220> FEATURE:
<223> OTHER INFORMATION: Peptide construct

<400> SEQUENCE: 90

Asp Gly Gln Glu Glu Lys Ala Gly Val Val Ser Thr Gly Leu Ile Gly
1               5                   10                  15

Gly Gly Ser Gly Gly Gly Ser Ser Leu Tyr Asn Thr Val Ala Thr Leu
            20                  25                  30

Tyr Ser Val His Gln Arg Ile Asp Val Lys Asp Thr Lys Glu Ala Leu
            35                  40                  45

Glu Lys Ile Glu Glu Glu Gln Asn Lys Ser
```

```
                        50                  55

<210> SEQ ID NO 91
<211> LENGTH: 65
<212> TYPE: PRT
<213> ORGANISM: Artificial Sequence
<220> FEATURE:
<223> OTHER INFORMATION: Peptide construct

<400> SEQUENCE: 91

Asp Gly Gln Glu Glu Lys Ala Gly Val Val Ser Thr Gly Leu Ile Gly
 1               5                  10                  15

Gly Gly Gly Ser Gly Gly Gly Ser Gly Gly Gly Ser Ser Leu
            20                  25                  30

Tyr Asn Thr Val Ala Thr Leu Tyr Ser Val His Gln Arg Ile Asp Val
            35                  40                  45

Lys Asp Thr Lys Glu Ala Leu Glu Lys Ile Glu Glu Gln Asn Lys
        50                  55                  60

Ser
65

<210> SEQ ID NO 92
<211> LENGTH: 56
<212> TYPE: PRT
<213> ORGANISM: Artificial Sequence
<220> FEATURE:
<223> OTHER INFORMATION: Peptide construct

<400> SEQUENCE: 92

Asp Gly Gln Glu Glu Lys Ala Gly Val Val Ser Thr Gly Leu Ile Gly
 1               5                  10                  15

Gly Gly Gly Ser Ser Ser Leu Tyr Asn Thr Val Ala Thr Leu Tyr Ser
            20                  25                  30

Val His Gln Arg Ile Asp Val Lys Asp Thr Lys Glu Ala Leu Glu Lys
            35                  40                  45

Ile Glu Glu Gln Asn Lys Ser
        50                  55

<210> SEQ ID NO 93
<211> LENGTH: 8
<212> TYPE: PRT
<213> ORGANISM: Artificial Sequence
<220> FEATURE:
<223> OTHER INFORMATION: Peptide construct

<400> SEQUENCE: 93

Gly Gly Gly Ser Gly Gly Gly Ser
 1               5

<210> SEQ ID NO 94
<211> LENGTH: 15
<212> TYPE: PRT
<213> ORGANISM: Artificial Sequence
<220> FEATURE:
<223> OTHER INFORMATION: Peptide construct

<400> SEQUENCE: 94

Gly Gly Gly Gly Ser Gly Gly Gly Gly Ser Gly Gly Gly Gly Ser
 1               5                  10                  15

<210> SEQ ID NO 95
<211> LENGTH: 8
<212> TYPE: PRT
```

```
<213> ORGANISM: Artificial Sequence
<220> FEATURE:
<223> OTHER INFORMATION: Peptide construct

<400> SEQUENCE: 95

Gly Gly Gly Ser Gly Gly Ser Ser
1               5

<210> SEQ ID NO 96
<211> LENGTH: 10
<212> TYPE: PRT
<213> ORGANISM: Artificial Sequence
<220> FEATURE:
<223> OTHER INFORMATION: Peptide construct

<400> SEQUENCE: 96

Gly Gly Gly Gly Ser Gly Gly Gly Gly Ser
1               5                   10
```

T CELL BINDING LIGAND PEPTIDES AND METHOD OF INDUCING A CELLULAR IMMUNE RESPONSE

CROSS REFERENCE TO RELATED APPLICATION

This application claims priority from PCT application PCT/US01/16793 filed May 24, 2001, published on Nov. 29, 2001, which in turn claims priority from U.S. Provisional Application Ser. No. 60/206,548 filed May 24, 2000.

FIELD OF THE INVENTION

This invention relates to peptide constructs useful in modulating the immune system of humans and other mammals, and to a peptide useful as a T cell binding ligand (TCBL) for directing a CD4 related T helper cell response, when the TCBL is linked to a disease associated antigenic peptide to form the peptide conjugate. More particularly, this invention relates to a derivative of Peptide G (the fifteen-mer peptide sequence from MHC IIβ chain (135-149), previously used as a T cell binding ligand for forming immunogenic peptide constructs, and which derivative enhances the immune response of immunogenic peptide constructs as compared to the same peptide conjugates but in which the non-derivatized Peptide G is used. In particular, this invention relates to an immunogenic composition useful to activate the immune system of a patient exposed to or at risk of infection by human immunodeficiency virus (HIV-1) which is the causative organism of the disease known as Acquired Immune Deficiency Syndrome (AIDS). This invention also relates to other peptide constructs for treating other specific immunological disorders and diseases and to the methods for treating individual subjects to modify the subjects immune system response.

DISCUSSION OF THE PRIOR ART

One of the present inventors has previously discovered a class of immunologically active and diagnostic peptide constructs obtained by joining one or more T cell binding ligands with an antigenic peptide. These peptide constructs are described in, for example, U.S. Pat. No. 5,652,342, the entire disclosure of which is incorporated herein, in its entirety, by reference thereto. These peptide constructs have been referred to by the assignee of the aforementioned patent by the trademark, L.E.A.P.S.™, an acronym for the coined expression, "Ligand Epitope Antigen Presentation System." More recently, specific classes of peptide constructs, based on the L.E.A.P.S. technology, have been developed for a number of specific immunological disorders, including, for example, HIV-1 (e.g., Ser. No. 08/695,304,), HSV (e.g., PCT/US98/20681), autoimmune disease (e.g., Ser. No. 60/161,734), the disclosures of which are incorporated herein in their entireties.

As described in these prior patent documents, linking of a T cell binding ligand to a peptide epitope could alter the nature of the immune response (i.e., cell mediated (TH1)— CD4 related TH1 or antibody (TH2)). It was further shown that the antibodies derived from certain conjugated peptides were better able to recognize the native molecule than were the antibodies prepared using a conventional peptide-KLH conjugate. It was shown that antibodies induced by the conjugated peptide (also referred to as "peptide construct") had a broader specificity, so that they recognized the peptide epitope not only in the free linear peptide form, but also in the native molecule. In some cases, the use of the peptide conjugated to KLH was not able to recognize the epitope in the native molecule.

As exemplary of the T cell binding ligand portion of the above described peptide constructs, a portion of the MHC Class II β from residues 135–149 (Peptide G) was used and achieved good results. The long range stability of the peptide constructs formed using Peptide G, was carried out with the construct dissolved in saline (0.15 M NaCl, pH 7.4) or in water for injection (WFI) at a concentration of 0.5–2.0 mg/ml and stored frozen soon after preparation. It was noticed (using HPLC methods applied to the above construct solutions maintained at temperatures of 2–8° C., i.e., refrigerated; or 18–25° C., i.e., room temperature; or 40° C., i.e., elevated, over periods of hours to days, and at pH values of from 7.4 down to 4.5) that the peptide constructs are prone to a deamination reaction, especially prevalent at more alkaline (higher) pH's. The deamination was observed at the amino terminus and yielded either an isoaspartic or aspartic acid residue at the N terminus.

Accordingly, further improvements in the long term stabilization of the conjugated peptides are desirable to enhance the value of these immunomodulators. In addition, new peptide constructs based on this modified TCBL and other TCBLs, for modulating the immune system of individual subject are desired.

SUMMARY OF THE INVENTION

The present invention is based, in part, on the discovery that a modified version of Peptide G (Asn Gly Gln Glu Glu Lys Ala Gly Val Val Ser Thr Gly Leu Ile—SEQ ID NO:2) obtained by replacing Asn with Asp to form Peptide G' (Asp Gly Gln Glu Glu Lys Ala Gly Val Val Ser Thr Gly Leu Ile—SEQ ID NO:1) overcomes the long range stabilization problem of the peptide conjugates and, quite surprisingly, also enhances the immune response, particularly the CD4 related (cell mediated) response, of conjugated peptides (L.E.A.P.S. constructs) as previously described.

Accordingly, in one aspect, the present invention provides a novel peptide having SEQ ID NO:1, useful as a TCBL in forming conjugated peptides having immunological activity by directing a host to mount a Th1 response to an antigenic peptide present in the peptide construct.

According to another aspect, the present invention also provides conjugated peptide constructs obtained by covalently bonding the peptide having SEQ ID NO: 1, directly, or preferably via a divalent linking group, to an antigenic peptide.

In accordance with still another aspect of the invention, there is provided a pharmacologically effective composition obtained from the above mentioned peptide construct and a pharmaceutically acceptable carrier.

In yet another aspect of the invention, there are provided new peptide constructs obtained by linking Peptide J (Asp Leu Leu Lys Asn Gly Glu Arg Ile Glu Lys Val Glu—SEQ ID NO:34) to various antigenic Cancer Muc1 peptides, CEA peptides, and others, and useful to modulate the immune response of individual subjects in need thereof.

This invention also provides a method for treating a patient suffering from an immunological disorder by administering to the patient a therapeutically effective amount of a peptide construct in which a peptide having SEQ ID NO:1 or SEQ ID NO:34 is covalently bonded to an antigenic peptide associated with the immunological disorder.

In accordance with a specific embodiment, the present invention relates to a peptide construct comprising a first T cell specific binding peptide having SEQ ID NO:1 and a second peptide covalently linked together, wherein the second peptide is an antigenic peptide of from about 25 to about 37 amino acids (which is referred to hereinafter as "modified HGP-30") and which is capable of eliciting preferentially TH1 associated antibodies when administered to a human in need thereof. The antigenic or second peptide has sequence identity (including naturally occurring variants and alleles thereof) with the p17 gag protein of HIV-1 wherein the peptide has a sequence originating with an amino acid residue chosen from residues 76 to 83 and ending with an amino acid residue chosen from residues 107 to 112 of p17 gag protein of HIV-1. In particular, the second or antigenic peptides disclosed in the aforementioned copending application Ser. No. 08/695,304, or copending application Ser. No. 08/695,301, the disclosures of which are incorporated herein in their entirety by reference thereto.

Peptide G', used as T cell specific binding molecule in the conjugated peptides of this invention will bind specifically or at least preferentially to specific class or subclass of T cells, such as helper T cells, $T_h$, suppressor T cells, $T_s$, cytotoxic T cells, CTL, and the like.

The second or antigenic peptide used to form the peptide construct of this invention, may be any known or subsequently discovered antigenic peptide, including, for example, any of the antigenic peptides mentioned in any of the above patents or copending patent applications, including, without limitation, peptides associated with herpes simplex virus (HSV), malaria, tuberculosis, cancers, AIDS, allergies, autoimmune diseases, such as, arthritis, Graves disease, multiple sclerosis (MS), myocarditis, diabetes, Lupus, and the like.

In accordance with a preferred aspect of the invention, the antigenic peptide is a portion of p17 of human immunodeficiency virus (HIV-1) and, particularly, a peptide of from about 25 to 37 amino acids, extending in the range from residues 76 to 112, such as the amino acid sequences shown by the following representative cases:

```
A T L   Y S V H Q R   I D V K D T   (SEQ ID NO:3)
K E A   L E K I E E   E

S L Y   N T V A T L   Y S V H Q R   (SEQ ID NO:4)
I D V   K D T K E A   L E K I E E
E Q N   K S K

R S L   Y N T V A T   L Y S V H Q   (SEQ ID NO:5)
R I D   V K D T K E   A L E K I E
E E Q   N K S K
```

In any of these sequences of modified HGP-30, it will be understood that one or more additional amino acids in the sequence from residues 76 to 112 may be added at either the N- or C-terminal, and similarly, one or more amino acids may be deleted from either terminal, while maintaining the total length from about 25 to about 37 amino acids.

A particularly preferred antigenic peptide for use in this invention has the following amino acid sequence

```
A T L   Y S V H Q R   I D V K D T   (SEQ ID NO:6)
K E A   L E K I E E   E Q N K S
```

SEQ ID NO:6, (sometimes referred to, for convenience, as m-HGP-30, or even more simply as "mH"), representing a modified version of HGP-30 (see, e.g., U.S. Pat. No. 4,983, 387).

While the following discussion will focus primarily on the conjugated peptides containing the sequence of Peptide G' and the sequence for a modified HGP-30, it is to be understood that other antigenic peptides, whether from HIV-1, HIV-2, or other disease causing organism, or antigenic peptide associated with a particular disease, disorder or condition, may be used in place of modified HGP-30 with expectation of similar results.

The conjugated peptides formed from Peptide G' and a modified HGP-30 offer the advantages previously seen with other conjugated peptides, such as those more generally disclosed in the aforementioned U.S. Pat. No. 5,652,342, of inducing broad spectrum antibodies but, additionally providing a desired TH1 specificity believed to result from the second or antigenic peptide which incorporates a CTL epitope which may modify the response to the desired isotype.

The present invention also relates to pharmaceutically effective compositions containing such antigen-peptide G' constructs (for convenience, may sometimes be referred to as "heteroconjugate") for eliciting immunization to infection against Human Immunodeficiency virus, HIV-1, in a human subject. Such compositions, in addition to the heteroconjugate of this invention will, preferably, include suitable immunological adjuvant(s).

Similarly, the invention relates to the use of such heteroconjugate and the pharmaceutically effective composition containing same for treating or preventing HIV-1 infection and Acquired Immunodeficiency Complex (AIDS) by administering to a human patient in need thereof, a therapeutically or prophylactively effective amount of the heterofunctional conjugate as defined above.

DETAILED DESCRIPTION OF THE INVENTION AND PREFERRED EMBODIMENTS

For the peptides disclosed in this application, the amino acid sequences thereof, are set forth by the single letter and three-letter identification symbols as follows:

| Amino Acid | Three-letter abbreviation | One-letter symbol |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

In particular, in accordance with one specific embodiment of the invention, pertaining to peptide constructs useful for improving the immune system of individuals exposed to, infected by, or at risk for exposure to the AIDS virus, the antigenic peptides useful in this invention will generally be between about 25 and 37 amino acids, as represented in the following exemplary cases including examples of a longer and shorter antigenic peptides:

```
A T L   Y S V   H Q R   I D V   K D T   (SEQ ID NO:3)
K E A   L E K   I E E   E

S L Y   N T V   A T L   Y S V   H Q R   (SEQ ID NO:4)
I D V   K D T   K E A   L E K   I E E
E Q N   K S K

R S L   Y N T   V A T   L Y S   V H Q   (SEQ ID NO:5)
R I D   V K D   T K E   A L E   K I E
E E Q   N K S   K
``` m-HGP-30 (mH) having the following sequence is especially preferred:

Ala Thr Leu Tyr Ser Val His Gln Arg Ile Asp Val Lys Asp Thr Lys Glu Ala Leu Glu Lys Ile Glu Glu Gln Asn Lys Ser or, using the corresponding single letter identifiers:

ATL YSV HQR IDV KDT KEA LEK IEE EQN KS(SEQ ID NO:6)

It should be understood that in any of the above amino acid sequences of antigenic peptides, variations of specific amino acids which do not adversely effect the desired biological activity are contemplated and included within the scope of the invention. In particular, it is recognized that the foregoing sequences are based upon a specific variant of HIV-1, namely, HIV-1 SF2 (actually, the Ser$^{86}$ analog of the natural Cys$^{86}$ sequence) and, although this region of interest of HIV-1 is generally fairly highly conserved, other naturally occurring and spontaneously occurring variants, including from one or several (e.g., up to about 10) variations of the amino acids are within the sequences of interest. Such natural and spontaneously occurring amino acid variations are specifically contemplated and, in certain cases, it may be advantageous to use mixtures of peptides, the sequences of which, may, correspond to two or more natural and spontaneously occurring variants of HIV-1.

Still further, as well recognized in the art, it is often advantageous to make specific amino acid substitutions in order, for example, to provide specific binding sites or for purpose of introducing a label, e.g., radioactive or fluorescent tagging, of the peptide. Such "designed" amino acid sequences are also within the scope of the antigenic peptides (e.g., modified HGP-30) of this invention.

Examples of different consensus sequences of HIV-1 which are also specifically included within the scope of the modified HGP-30 antigenic peptides for use as the second peptide in the conjugated peptides of this invention include, for instance, the following, taken from "HIV-1 Sequence Database, Human Retroviruses and AIDS 1996: A Compilation and Analysis of Nucleic Acid and Amino Acid Sequences", edited by G. Myers, et al., Theoretical Biology and Biophysics Group, Los Alamos National Laboratory, Los Alamos, N.M., December 1996, and any of the subsequent yearly updates thereof. The lower case letters represent potential or known cites of amino acid variability resulting from the allelic variations, genetic drift and mutations of the particular consensus sequence; the presence of a "?" symbol reflects that there was, at the time of publication, no agreed upon consensus for the amino acid at that position of the consensus sequence:

```
CONSENSUS A:
kSL fNt vat Lyc vHq rId          SEQ ID NO:7
vkD tKe Ald kiE eiq nKs k CONSENSUS B:
rSL yNt vat Lyc vHq rIe          SEQ ID NO:8
vkD tKe Ald kiE eEq nKs k CONSENSUS C:
rSL ?Nt vat LyC vH? ?Ie          SEQ ID NO:9
vrD tKe Ald kiE eEq nK?Q CONSENSUS D:
kSL ?Nt vat Lyc vHe rIe          SEQ ID NO:10
vkD tKe Ale kmE eEq nKs k CONSENSUS F:
rSL yNt vav Lyf vHq rvE          SEQ ID NO:11
vkD tKe Ald KLE eEq nKs q CONSENSUS G:
kSL ?N? ?a? L?c ?Hq rIe          SEQ ID NO:12
vkD tKe Ale EVE Kaq kns Q CONSENSUS H:
QSL fNL La? Lyc vHq rId          SEQ ID NO:13
?kD tKe Al? k?? e?q n?? Q CONSENSUS O:
?SL WNA I?V LWc vHN r??          SEQ ID NO:14
I?D tQQ AIQ kLK eVM ?sR K
```

A "most likely" sequence over the region of interest, transcending the different subtypes is also given in the 1996 publication, as follows:

KSL FNT VAV LYC VHQ RIE VKD TKE ALD K.
SEQ ID NO: 15

Sequences of, and identification of, specific species within each of these subtypes are available in the published literature, including not only the 1996 Myers, et al, publication, supra, but also, other annual Los Alamos Compendia, including Human Retroviruses and AIDS 1999: A Compilation and Analysis of Nucleic Acid and Amino Acid Sequences, CL Kuiken, et al, Eds., Theoretical Biology and Biophysics Group, Los Alamos National Laboratory, Los Alamos, N.Mex., 1999. These databases, such as, "HIV-1 Sequence Database, 1998/1999 HIV-1 and SIV alignments," are available on the Internet at web site (URL): http://hiv-web.lanl.gov which includes a link to: http://hiv-web.lanl.gov/ALIGN_CURRENT/00get_align.cgi, the latter including sequences for many different subtypes of HIV-1, the disclosure of which is incorporated herein by reference thereto, and a copy of which is appended to this application.

Any of these or other naturally occurring species within Consensus A, Consensus B, Consensus C, Consensus D, as well as Consensus F, Consensus G, Consensus H, Consensus O, whether presently known or existing, or subsequently discovered or subsequently arising, can be used as the modified HGP-30 antigenic peptide in the peptide constructs of this invention. It is well known in the art that these various consensus sequences are generally derived from, and are prevalent in different geographical regions of the world and are often referred to as "clades" (also known as "subtypes") of the HIV-1 virus.

Representative of these clades of modified HGP-30 include the following consensus sequences (wherein the letter designations generally correspond to the consensus sequences as given above) and any allelic variations thereof:

```
                                               SEQ ID NO:16
Thailand-B:
YCV HQK IEV KDT KEA LEK IEE EQN KSK KKA SEQ ID NO:17
Thailand-A/E:
WCV HQR IEV KDT KEA LDK IEE VQN KSQ QKT SEQ ID NO:18
Uganda-A:
YCV HQR IDV KDT KEA LNK IEE MQN KNK QRT SEQ ID NO:19
Kenya-A:
YCV HQR IDV KDT KEA LDK IEE IQN KSK QKT SEQ ID NO:20
Brazil-A/E:
YFV HQR VEV KDT KEA LDK LEE EQN KSQ QKT SEQ ID NO:21
Brazil-B:
YCV HQK IDV RDT KEA LEK VEE EQN KSK EKA SEQ ID NO:22
Uganda-B:
YCV HQR IDV KDT KEA LDK IEE EQN KSK KKE SEQ ID NO:23
Uganda-C:
YCV HKG IEV RDT KEA LDK IEE EQN KIQ QKT SEQ ID NO:24
India-C:
YCV H?? IEV RDT KEA LDK IEE EQN K?Q QKT SEQ ID NO:25
Uganda-D:
YCV HER IKV ADT KEA LDK IEE EQT KSK KKA
```

As can be seen from the above aligned consensus sequences and species for the various consensus sequences, there is some variation amongst HIV-1 subtypes in the gag protein sequence. Moreover, there is considerable variation in the specific numbering of amino acids among different HIV-1 strains. In the present invention, the numbering of sequences is based on the sequence of clade B HIV-1 strain SF2 or MN (most recently revised to MNCG); however, it is the amino acid sequence itself, allowing for variations observed amongst HIV-1 subtypes, that is important. The sequences as described above and in the appended literature are illustrative of the types of amino acid changes that can be made in the antigenic modified HGP-30 peptides of the invention and the conjugated peptides based thereon.

In particular HIV-1 SF2 (Clade B) has the following sequence in the region from residue 76 to residue 112:

```
    RSL YNT VAT LYC VHQ RID VKD TKE ALE KIE EEK QKS
        K                                          SEQ ID NO:26
``` while HIV-1 MNCG (Clade B) has the following sequence in the region from residue 76 to residue 112:

```
    KSL YNT VAT LYC VHQ KIE IKD TKE ALE
        KIE EEQ NKS K                              SEQ ID NO:27
```

In addition to the variations in the amino acids among the various HIV-1 strains, it is also recognized that the amino acids at the N-terminal and C-terminal may be present as the free acid (amino or carboxyl groups) or as the salts, esters, ethers, or amides thereof. In particular amide end groups at the C-terminal and acetylation, e.g., myristyl, etc. at the N- or C-terminal, are often useful without effecting the immunological properties of the peptide.

The conjugated peptides and the constituent components thereof can be prepared by conventional processes for synthesizing proteins, such as, for example, solid phase peptide synthesis, as described by Merrifield, R. B., 1963, J. of Am. Chem. Soc., 85:2149–2154. It is also within the scope of the invention and within the skill in the art to produce the novel peptide constructs of this invention or the peptide components thereof by genetic engineering technology.

In the present invention, the above modified HGP-30 antigenic peptides are covalently linked to Peptide G'.

Peptide constructs prepared by linking the antigenic peptides based on the modified HGP-30 epitopes to Peptide G' have been shown by the inventors to elicit an immune response to HIV-1 that can be directed toward the desired TH1 response as evidenced by the numerous examples of the TH1 characteristic antibody IgG2a (mouse) or IgG3 (man) induction. The order of Peptide G' and second modified HGP-30 peptide is not usually critical and may be reversed. For example, if modified HGP-30 (B) is linked to G' then the peptide construct may have the sequence G'-B or B-G'. Also, while Peptide G' and modified HGP-30 may be directly coupled to each other, it is preferred that a small linker sequence or a larger heterolinker molecule may be used to couple the two peptides. For example, as the spacer, one or a few, up to about 5, preferably, up to about 3 or 4, neutral amino acids, such as glycine, may be used to link the peptides. Preferred spacer peptides include, for example, GGG, and GGGGS, however, the spacer may be made larger or smaller and altered to include other molecules or amino acids, besides the amino acid glycine, such as in GGGGS. Examples of other known spacers which may be used for covalently linking two or more peptides or proteins or equivalent DNA sequences, include, for example, GGGSGGGS (SEQ ID NO:93); GGGGSGGGGSGGGGS (SEQ ID NO:94); GGGGSS (SEQ ID NO:28); GGGGSGGGGSGG (SEQ ID NO:29); GGGSGTGSGSGS (SEQ ID NO:30); GGGGSGGGSGGGS (SEQ ID NO:31); KGKGKGL (SEQ ID NO:32) and VAKLEAKVAK-LEAKGKGKY (SEQ ID NO:33).

As examples of heterolinkers mention may be made of, for example, N-succinimidyl-3-(2-pyridylthio)propionate (SPDP), m-maleimidobenzoyl-N-hydroxy-succimide (MBS) as well as any of the other reagents employed to link peptides, including without limitation those disclosed in the aforementioned U.S. Pat. No. 5,652,342.

The administration of the peptide constructs of this invention may be carried out alone or in conjunction with other therapy. Examples of other therapies which may be used in conjunction with the peptide constructs of this invention include, in the case of treatments (prophylactic or therapeutic) for infection by HIV-1, for example, protease inhibitors, reverse transcriptase inhibitors, zinc binding inhibitors, and the like.

The peptide constructs of this invention, may be represented by formula (I):

$$\text{Peptide G'-x-P*} \qquad (I)$$

wherein Peptide G' is the peptide having SEQ ID NO:1 x is a direct bond or divalent linking group; and

P* is an antigenic peptide associated with AIDS, especially HIV-1.

The conjugated peptides of formula (I) may be used to direct the immune response prophylactically (e.g., to a CD4 directed immune response) to prevent infection or reduce the likelihood of infection by HIV-1, or to direct the immune response therapeutically (e.g., to a TH1 directed immune response) in HIV-1 infected individuals, perhaps in conjunction with other therapies, to reduce viral load and to control or cure the infection by HIV-1. The peptide constructs may also be used to direct the immune response prophylactically to induce a TH1 (cellular), TH2 (antibody) or mixed TH1/TH2 directed immune response to prevent or reduce the infection by HIV-1, or to direct the immune response therapeutically to induce a TH1, e.g., $CD4^+$, TH2 or mixed TH1/TH2 directed immune response against the AIDS virus, perhaps in conjunction with other therapies to reduce the viral load and to control or cure the infection by HIV-1 in HIV-1 infected subjects.

The peptide constructs of this invention may be used as a component of an immunomodulatory composition, together with one or more pharmaceutically acceptable carriers or adjuvants, either prophylactically or therapeutically. When provided for use prophylactically, the immunomodulatory composition is provided in advance of any evidence of infection by HIV-1. The prophylactic administration of the composition should serve to prevent or attenuate HIV-1 in mammals. In a preferred embodiment a human, at high risk for HIV-1 is prophylactically treated with the peptide conjugate of this invention, as such, or as a component of an immunomodulatory composition. When provided therapeutically, the peptide construct or composition containing same is provided to enhance the HIV-1 infected patient's own immune response to the HIV-1 antigen.

The peptide construct is, in the case of treatments for individuals exposed to the AIDS virus, preferably administered after disease symptoms and viral load have been reduced or stabilized by Highly Active AntiRetroviral therapy (HAART).

While it is possible for the immunogenic peptide construct to be administered in a pure or substantially pure form, it is preferable to present it as a pharmaceutical composition, formulation or preparation.

The formulations of the present invention, both for clinical and for human use, comprise a conjugated peptide as described above, together with one or more pharmaceutically acceptable carriers and, optionally, other therapeutic ingredients, especially therapeutic immunological adjuvants. The carrier(s) must be "acceptable" in the sense of being compatible with the other ingredients of the formulation and not deleterious to the recipient thereof. The formulations may conveniently be presented in unit dosage form and may be prepared by any method well-known in the pharmaceutical art.

In general, the formulations are prepared by uniformly and intimately bringing into association the active ingredient with liquid carriers or finely divided solid carriers or both, and then, if necessary, bringing the product into the desired formulation.

Formulations suitable for intravenous, intramuscular, subcutaneous, or intraperitoneal administration conveniently comprise sterile aqueous solutions of the active ingredient(s) with solutions which are preferably isotonic with the blood of the recipient. Such formulations may be conveniently prepared by dissolving solid active ingredient in water containing physiologically compatible substances such as sodium chloride (e.g. 0.1–2.0M), glycine, and the like, and having a buffered pH compatible with physiological conditions to produce an aqueous solution, and rendering the solution sterile. These may be present in unit or multi-dose containers, for example, sealed ampoules or vials.

The formulations of the present invention may incorporate a stabilizer or excipient. Illustrative excipients include polyethylene glycol, glycerol, proteins, saccharides, amino acids, inorganic acids, and organic acids which may be used either on their own or as admixtures. These excipients, when used, are preferably incorporated in an amount of about 0.1 to about 10,000 parts by weight per part by weight of immunogen. If two or more stabilizers are to be used, their total amount is preferably within the range specified above. These excipients are used in aqueous solutions at the appropriate concentration and pH. The specific osmotic pressure of such aqueous solutions is generally in the range of about 0.1 to about 3.0 osmoles, preferably in the range of about 0.8 to about 1.2. The pH of the aqueous solution is adjusted to be within the range of about 5.0 to about 9.0, preferably within the range of 6–8. In formulating the immunogenic conjugated peptide of the present invention, anti-adsorption agent may be used.

Additional pharmaceutical methods may be employed to control the duration of action. Controlled release preparations may be achieved through the use of polymer to complex or absorb the conjugated peptide. The controlled delivery may be exercised by selecting appropriate macromolecules (for example polyester, polyamino acids, polyvinyl, pyrrolidone, ethylenevinylacetate, methylcellulose, carboxymethylcellulose, or protamine sulfate) and the concentration of macromolecules as well as the methods of incorporation in order to control release.

Another possible method to control the duration of action by controlled-release preparations is to incorporate the conjugated peptide into particles of a polymeric material such as polyesters, polyamino acids, hydrogels, poly(lactic acid) or ethylene vinylacetate copolymers.

Alternatively, instead of incorporating these agents into polymeric particles, it is possible to entrap these materials in microcapsules prepared, for example, by coacervation techniques or by interfacial polymerization, for example, hydroxy-methylcellulose or gelatin-microcapsules and poly (methylmethacrylate) microcapsules, respectively, or in colloidal drug delivery systems, for example, liposomes, albumin microspheres, microemulsions, nanoparticles, and nanocapsules or in macroemulsions.

When oral preparations are desired, the compositions may be combined with typical carriers, such as lactose, sucrose, starch, talc, magnesium stearate, crystalline cellulose, methyl cellulose, carboxymethyl cellulose, glycerin, sodium alginate or gum arabic among others.

The peptide constructs of the present invention may be supplied in the form of a kit, alone, or in the form of a pharmaceutical composition as described above.

Administration of the peptide constructs and immunomodulatory compositions containing same can be conducted by conventional methods. For example, the immunogenic peptide construct can be used in a suitable diluent such as saline or water, or complete or incomplete adjuvants. The immunogen can be administered by any route appropriate for immune system stimulation, such as intravenous, intraperitoneal, intramuscular, subcutaneous, nasal, oral, rectal, vaginal, and the like. The immunogen may be administered once or at periodic intervals until, for example, a significant titer of $CD4^+$ or $CD8^+$ T cell and/or antibodies directed against the HIV-1 antigen is obtained. In particular, the antigenic peptide constructs of the invention elicit TH1 associated antibodies and other aspects of a TH1 immune response. The presence of such cells may be assessed by measuring cytokine secretion specific for TH-1 (e.g., IFN-γ, IL-2) or TH-2 (e.g., IL-4, IL-10) in response to being pulsed with the immunogen. The antibody may be detected in the serum using conventional immunoassays.

As noted above, the administration of the peptide constructs of the present invention and the immunomodulatory compositions containing same may be for either a prophylactic or therapeutic purpose. When provided prophylactically, the immunogen is provided in advance of any evidence or in advance of any symptom due to HIV-1, or other disease causing organism, especially in patients at significant risk for occurrence. The prophylactic administration of the immunogen serves to prevent or attenuate HIV-1, or other disease or condition associated with the antigenic peptide component of the conjugated peptide in a human or other animal. When provided therapeutically, the immunogen is provided at (or after) the onset of the disease or at the onset of any symptom of the disease. The therapeutic administration of the immunogen serves to attenuate the disease.

The invention also concerns a method for treating or preventing human acquired immunodeficiency syndrome (AIDS) caused by infection with HIV-1, by administering to a human patient in need thereof a therapeutically effective amount of the peptide construct of this invention, such as the peptide construct of formula (I), wherein the antigenic peptide P* is an antigen associated with AIDS, especially, one of the antigenic peptides from p17, as previously described.

Similarly, for treatment of other disease, condition or disorder, the antigenic peptide P*, will be chosen from the antigenic peptides associated with or causing the particular disease, disorder or condition, such as previously described, for example, in U.S. Pat. No. 5,652,342, or any of the other copending applications described above, or any other of the myriad known antigenic peptides associated with disease or causing disease.

In this regard, peptide constructs of the following formula (II) are also provided by the present invention:

$$P^1\text{-}x\text{-}P^2 \qquad (II)$$

where $P^1$ represents the peptide having SEQ ID NO:1 or SEQ ID NO:34;

x represents a direct bond or divalent linking group; and $P^2$ represents a peptide associated with disease, including immunological disorders, autoimmune diseases, and conditions;

As non-limiting examples of other antigenic peptides represented by $P^2$ mention may be made of, for example, antigenic peptides associated with autoimmune myocarditis, such as Peptide My: DSA FDV LSF TAE EKA GVY K (SEQ ID NO:42);

antigenic peptides associated with cancer, especially Muc1, such as M1a, having the sequence APD TRP AP (SEQ ID NO:43); M1b, having the sequence STA PPA HGV (SEQ ID NO:44); M1c, having the sequence GVT SAP DTR PAP GST APP AH (SEQ ID NO:45);

CEA antigenic peptides, such as, for example:

| C1: | YSL GAN LNL | (SEQ ID NO:46) |
| C2: | EAQ NTT YL | (SEQ ID NO:47) |
| C3: | QYS WFV NGT F | (SEQ ID NO:48) |
| C4: | TYA CFV SNL | (SEQ ID NO:49) |
| C5: | IYP NAS LLI; | (SEQ ID NO:50) | antigenic peptides associated with Herpes Simplex Virus, such as, for example, gD1$_{8-23}$:
SLK MAD PNR FRG KDL P         (SEQ ID NO:51)

gD1$_{1-23}$:
KYA LAD ASL KMA DPN RFR GKD LP; (SEQ ID NO:52)

extgB1:
ERI KTT SSI EFA RLQ FTT DHI Q;  (SEQ ID NO:53)

antigenic peptides associated with HIV-1, including not only those previously described, but also those associated with p24, GP41, GP120, or GP160.

The divalent linking group x may be a direct bond or any of the divalent linking groups or spacers as previously described.

As examples of peptide constructs according to formula (II), mention is made of the following representative examples:

```
                                      (SEQ ID NO:54)
    DGQ EEK AGV VST GLI GGG APD TRP AP (SEQ ID NO:55)
    DGQ EEK AGV VST GLI GGG STA PPA HGV (SEQ ID NO:56)
    DGQ EEK AGV VST GLI GGG GVT SAP DTR
        PAP GST APP AH (SEQ ID NO:57)
    DGQ EEK AGV VST GLI GGG YLS GAN LNL (SEQ ID NO:58)
    DGQ EEK AGV VST GLI GGG EAQ NTT YL (SEQ ID NO:59)
    DGQ EEK AGV VST GLI GGG QYS WFV NGT F (SEQ ID NO:60)
    DGQ EEK AGV VST GLI GGG TYA CFV SNL (SEQ ID NO:61)
    DGQ EEK AGV VST GLI GGG IYP NAS LLI (SEQ ID NO:62)
    DLL KNG ERI EKV EGG GAP DTR PAP (SEQ ID NO:63)
    DLL KNG ERI EKV EGG GST APP AHG V (SEQ ID NO:64)
    DLL KNG ERI EKV EGG GG VTS APD TRP
        APG STA PPA H (SEQ ID NO:65)
    DLL KNG ERI EKV EGG GYL SGA NLN L (SEQ ID NO:66)
    DLL KNG ERI EKV EGG GEA QNT TYL (SEQ ID NO:67)
    DLL KNG ERI EKV EGG GQY SWF VNG TF (SEQ ID NO:68)
    DLL KNG ERI EKV EGG GTY ACF VSN L (SEQ ID NO:69)
    DLL KNG ERI EKV EGG GIY PNA SLL I (SEQ ID NO:70)
    DGQ EEK AGV VST GLI GGG KYA LAD ASL
        KMA DPN RFR GKD LP
```

-continued

```
                                      (SEQ ID NO:71)
DLL KNG ERI EKV EGG GKY LAD ASL
    KMA DPN RFR GKD LP (SEQ ID NO:72)
DGQ EEK AGV VST GLI GGG SLK MAD PNR
    FRG KDL P (SEQ ID NO:73)
DLL KNG ERI EKV EGG GSL KMA DPN RFR
    GKD LP (SEQ ID NO:74)
DLL KNG ERI EKV EGG GLY RTF AGN PRA
    GGG KYA LAD ASL KMA DPN RFR GKD LP (SEQ ID NO:75)
DLL KNG ERI EKV EGG GER IKT TSS IEF ARL
    QFT TDH IQ (SEQ ID NO:76)
DGQ SEK AGV VST GLI GGG ERI KTT SSI EFA
    RLQ FTT DHI Q (SEQ ID NO:77)
DLL KNG ERI EKV EGG GAT LYS VHQ RID VKD
    TKE ALE KIE EQN KS (SEQ ID NO:78)
DLL KNG ERI EKV EGG GSG GGS ATL YSV HQR
    IDV KDT KEA LEK IEE EQN KS (SEQ ID NO:79)
DLL KNG ERI EKV EGG GGS GGG GSG GGG SAT
    LYS VHQ RID VKD TKE ALE KIE EEQ NKS (SEQ ID NO:80)
DLL KNG ERI EKV EGG GGS SAT LYS VHQ
    RID VKD TKE ALE KIE EEQ NKS (SEQ ID NO:81)
DGQ EEK AGV VST GLI GGG ATL YSV HQR IDV
    KDT KEA LEK IEE EQN KS (SEQ ID NO:82)
DGQ EEK AGV VST GLI GGG SGG GSA TLY SVH
    QRI DVK DTK EAL EKI EEE QNK S (SEQ ID NO:83)
DGQ EEK AGV VST GLI GGG GSG GGG SGG GGS
    ATL YSV HQR IDV KDT KEA LEK IEE EQN KS (SEQ ID NO:84)
DGQ EEK AGV VST GLI GGG GSS ATL YSV HQR
    IDV KDT KEA LEK IEE EQN KS (SEQ ID NO:85)
DLL KNG ERI EKV EGG GSL YNT VAT LYS VHQ
    RID VKD TKE ALE KIE EEQ NKS (SEQ ID NO:86)
DLL KNG ERI EKV EGG GSG GGS SLY NTV ATL
    YSV HQR IDV KDT KEA LEK IEE EQN KS (SEQ ID NO:87)
DLL KNG ERI EKV EGG GGS GGG GSG GGG SSL
    YNT VAT LYS VHQ RID VKD TKE ALE KIE
    EEQ NKS (SEQ ID NO:88)
DLL KNG ERI EKV EGG GGS SSL YNT VAT LYS
    VHQ RID VKD TKE ALE KIE EEQ NKS (SEQ ID NO:89)
DGQ EEK AGV VST GLI GGG SLY NTV ATL YSV
    HQR IDV KDT KEA LEK IEE EQN KS
```

```
                                      (SEQ ID NO:90)
DGQ EEK AGV VST GLI GGG SGG GSS LYN TVA
    TLY SVH QRI DVK DTK EAL EKI EEE QNK S (SEQ ID NO:91)
DGQ EEK AGV VST GLI GGG GSG GGG SGG GGS
    SLY NTV ATL YSV HQR IDV KDT KEA LEK
    IEE EQN KS (SEQ ID NO:92)
DGQ EEK AGV VST GLI GGG GSS SLY NTV ATL
    YSV HQR IDV KDT KEA LEK IEE EQN KS
```

According to this invention the immune response induced by the conjugated peptide is at least predominantly directed toward at least the desired TH1 response as evidenced by the TH1 characteristic antibody IgG2a (mouse) and presumably thereby IgG3 (man). These peptide conjugates may, however, in addition to a TH1 elicited immune response, elicit a TH2 immune response, and in particular, a mixed TH1/TH2 immune response.

Accordingly, the antigenic peptide constructs of this invention provide potentially powerful vaccines for preventing infection by, or treating cells infected by, HSV and many other infectious and viral diseases or other immunogenic disorders and conditions. Therefore, the present invention provides such vaccine compositions which can be used to immunize patients at risk for, or exposed to the causative organism associated with a particular disease or disorder, such as, HSV, and various forms of cancer.

The present invention, therefore, provides antigenic peptide constructs, which provide powerful vaccines for neutralizing and/or killing infected cells. Therefore, the vaccines of this invention can be used to immunize patients at risk for or exposed to various diseases (e.g., bacterial or viral caused diseases, e.g., herpes simplex virus, tuberculosis, diabetes, and the like) as well as other immunological disorders caused by exposure to an antigen, including, for example, allergies, asthma, autoimmune diseases, such as myocarditis, and the like.

When used as a vaccine in the method of this invention, the vaccine can be introduced into the host most conveniently by injection, intramuscularly, intradermally, parenterally, orally or subcutaneously. Any of the common liquid or solid vehicles may be employed, which are acceptable to the host and which do not have any adverse side effects on the host or any detrimental effects on the vaccine. Phosphate buffered saline (PBS), at physiological pH, e.g. pH 6.8 to 7.2, preferably pH 7, may be used as a carrier, alone or with a suitable adjuvant. The concentration of immunogenic peptide construct may vary from about 0.5 to 200 µg/kg, such as about 25 µg/kg per injection, in a volume of clinical medium (e.g., solvent) generally from about 0.1 to 1 ml, such as about 0.2 ml, preclinical studies in animals, and from about 0.5 ml to about 2 ml, such as about 1 ml in humans. Multiple injections may be required after the initial injections and may be given at intervals of from about 2 to 8 weeks, or other suitable time interval, for example, about 2 weeks in animals and about 8 weeks in humans, when multiple injections are given.

A preferred concentration of immunogenic peptide construct in the vaccines of the present invention may be in the range of from 10 to 25 µg/kg, however, a higher or lower dose may be administered as needed.

EXAMPLE 1

This example demonstrates the improved biological activity of peptide constructs according to the present invention in comparison to similar peptide constructs and conventional peptide-immunogenic carrier constructs.

I. Peptides

Peptide constructs were prepared using as T cell binding ligand, either Peptide G' (SEQ ID NO:1), Peptide G (SEQ ID NO:2), Peptide J, from a region of β-2 microglobulin (38–50)

```
        DLL KNG ERI EKV E               SEQ ID NO:34
``` or Peptide F, from IL-1β (163-171)

```
        VQG EES NDK                     SEQ ID NO:35.
``` or using a conventional immunogenic carrier protein, Keyhole Limpet Haemocyanin (KLH) (Biosyn).

The peptide constructs are prepared using Peptide J or Peptide F or Peptide G' or Peptide G with the modified HGP-30 having SEQ ID NO:6 (mH) or HGP-30 (YSVHQRIDVKDTKEALEKIEEEQNKSKKKA) (SEQ ID NO:36) and a spacer GGG (however, similar results would be obtained using a different spacer, e.g., GGGS, GGGSGGGS (SEQ ID NO:93), GGGGSGGGGSGGGGS (SEQ ID NO: 94); GGGSGGSS (SEQ ID NO:95), GGGGSGGGGS (SEQ ID NO:96), etc.).

Accordingly, the peptide constructs used in this example have the following formulas:

II. Preparation of KLH Conjugates

Keyhole Limpet Haemocyanin (KLH) (cGMP grade, Biosyn) is conjugated to m-HGP-30 (mH) peptide by a glutaraldehyde conjugation method using a 1:1 mg weight ratio of peptide to KLH.

The peptide constructs may be synthesized as a single peptide without any conjugation step or by conjugation of the T cell binding ligand peptide (G', G, F or J) and the antigenic peptide (e.g., mH or HGP-30) by using the thioether method or by any other conjugation method known to the skilled practitioner.

The final products (peptides, peptide constructs, peptide –KLH control), are analyzed for protein or peptide using the BCA protein, or other suitable, assay, and adjusted to contain between 200–400 μg/ml of total protein or peptide, and stored frozen (–20° C.) in suitable (e.g., 1.5 ml) aliquots ready for thawing and administered in combination with an adjuvant ISA-51 (Seppic) or microfluidized MPL S/E (Corixa).

III. Immunization and Assay Procedures

The procedure used is as described below.

Mice in groups (5-10 animals per group as designated) are immunized with the LEAPS constructs (25 μg/dose) of SEQ ID NO's:37, 38 and 39, in 0.2 mL emulsified 1:1 with adjuvant (Seppic's ISA-51 or Corixa's microfluidized MPL S/E) on days 0 and 14. Mice are evaluated by Delayed Type of Hypersensitivity (DTH) by inoculation on day 26 with 20 μl of a solution of saline or mH (SEQ ID NO:6) (25 μg in saline) in the left or right ear respectively. The DTH response is determined by measurement of the ear thickness 48 hours later and expressed as increase in ear thickness (mm) of experimental ear compared to that of the control ear. Individual animal sera are collected for measurement of antibody on day 28, 42, 63 and 77. Sera from individual animals and group pools are evaluated for specific anti-mH antibody, for total antibody, IgG1, IgG2a and IgG3 antibody isotype and cross clade titer at selected time points as indicated.

IV. Results

The results of an isotype analysis of day 42 test bleedings with G'-mH (SEQ ID NO:37), G-mH (SEQ ID NO:38), J-mH (SEQ ID NO:39), F-mH (SEQ ID NO:40) and F-HGP-30 (SEQ ID NO:41), are shown in Table 1. The G' construct resulted in significantly higher signals, indicative of higher levels of the TH1 preferred isotypes (IgG2a and IgGb2) relative to the TH2 isotypes (IgG1).

```
DGQ EEK AGV VST GLI GGG ATL YSV HQR IDV KDT KEA LEK IEE EQN KS   SEQ ID NO:37

NGQ EEK AGV VST GLI GGG ATL YSV HQR IDV KDT KEA LEK IEE EQN KS   SEQ ID NO:38

DLL KNG ERI EKV EGG GAT LYS VHQ RID VKD TKE ALE KIE EEQ NKS      SEQ ID NO:39

VQG EES NDK GGG ATL YSV HQR ICV KDT KEA LEK IEE EQN KS           SEQ ID NO:40
wherein the underlined portion represents mH (SEQ ID NO:6); and VQG EES NDK GGG YSV HQR IDV KDT KEA LEK IEE EQN KSK KKA          SEQ ID NO:41
where the double underlined portion represents HGP-30 (SEQ ID NO:36)
```

The peptides may be synthesized using, for example, the F-moc or t-Boc procedure and a double coupling protocol for the first 8 residues. Usually the peptide is prepared with the carboxyl terminus as an amide form. All of the peptides are purified using preparative HPLC, and analyzed by an analytical HPLC, amino acid analysis and mass spectrophotometer. The peptides are greater than 95%, usually greater than 98%, pure by HPLC criteria. The dry peptides are stored in vials with desiccant at –8° C.

Table 2 shows the results of the ELISA antibody screening of the sera from the above animals, but with test bleeding collected at day 63 and for cross clade recognition. The mouse sera for the ELISA was used at a dilution of 1:200. Again, clearly, the construct provides higher signals indicative of higher levels of the antibodies that recognized other clades besides the parental one (Clade B) of mH.

An isotype analysis for pools of day 28 test bleedings G-mH, G'-mH and m-HGP-30/KLH using either MPL S/E or ISA51 as adjuvant, are shown in Table 3. These results from another group of animals confirm the results in Table 1 and extend the observation by showing higher endpoint titers for the preferred isotypes.

A cross clade analysis for pools of day 42 test bleedings from the same groups as used in Table 3, were obtained and the results are shown in Table 4. Clearly the G' construct resulted in higher signals indicative of higher levels of the TH1 preferred antibody isotypes (IgG2a and IgG2b) relative to the TH2 antibody isotypes (IgG1). Again, clearly, the G' construct resulted in higher signals indicative of higher levels of the antibodies that recognized other clades besides the parental one (Clade B) of the mH, although not as strong as the KLH conjugates.

A specificity analysis for the TCBL or KLH carrier for pools of day 42 test bleedings from the G-mH, G'-mH and mH/KLH, using either MPL S/E or ISA51 as adjuvant, was carried out (all sera assayed at a dilution of 1:200) and the results are shown in Table 5. These results demonstrate that G' conjugates and the G conjugate showed minimal reactivity toward the delivery vehicle TCBL as contrasted to the KLH conjugates. This observation is especially significant for vaccines used on a repetitive basis, such as, either a vaccine that requires more frequent intervals between boosters for maintenance of cellular reactivity or as a therapeutic vaccine.

EXAMPLE 2

This example is designed to demonstrate "mechanism of action" as further "proof of principle" of the LEAPS technology. The analysis is based on use of peptide J with mH (SEQ ID NO:39) and Peptide G' with mH (SEQ ID NO:37), for mechanism and types of cells involved.

Select immunoglobulin preparations were obtained from Dr. Stephen Hoffmann, Malaria Program, U.S. Navy. These preparations were prepared using specialized monoclonal antibodies (anti CD4 or CD8) that allow the determination by depletion of the cell type that possess the markers the antibodies recognize. This allows one to determine some parts of the nature of various cellular (e.g., T-cell) involvement in the early stage of immune system response with the LEAPS peptide-constructs. It is recognized, however, that this is only a temporary event since new cells are continuously being developed from stem cells and the animals become resistant to the reagents.

The animals are pretreated with the antisera as indicated for 5 days before the initial immunization with peptide-construct having SEQ ID NO:37 or SEQ ID NO:39 on day 1. No pretreatment is done before the booster immunization on day 14 or DTH on day 26–28. The mice are then inoculated with the test antigen or saline (control) on day 26 in the left and right ears, respectively, and the DTH response is measured on day 28. The difference between the values for the test and saline control ears is calculated for each group of five animals along with the standard error of the mean (sem) and the results are plotted (see FIG. 1). Also shown in FIG. 1 are values for the untreated animals and animals immunized on day 14 only.

These initial results, as shown in FIG. 1, using the cell specific antisera as a depletion reagent (used to eliminate from the mouse functional cells that contain a specific surface marker) for the primary immunization, demonstrate that for a DTH response: (1) SEQ ID NO:37 construct requires the presence and presumably activation of CD4+ but not CD8+ cells, and (2) SEQ ID NO:59 construct containing a TCBL from β-2-microglobulin which is associated with MHC I, requires the presence and presumably activation of CD8+ but not CD4+ cells. The DTH (Delayed Type Hypersensitivity) data is statistically significant with a t-test of 0.05 for SEQ ID NO:39 and anti-CD8. The DTH for pretreatment of SEQ ID NO:37 immunized mice with anti-CD4 was just above the cutoff limit for statistical significance due to a weaker DTH response and small group size. Table 6 shows the same DTH data and provides additional experimental details.

EXAMPLE 3

Figure 2:
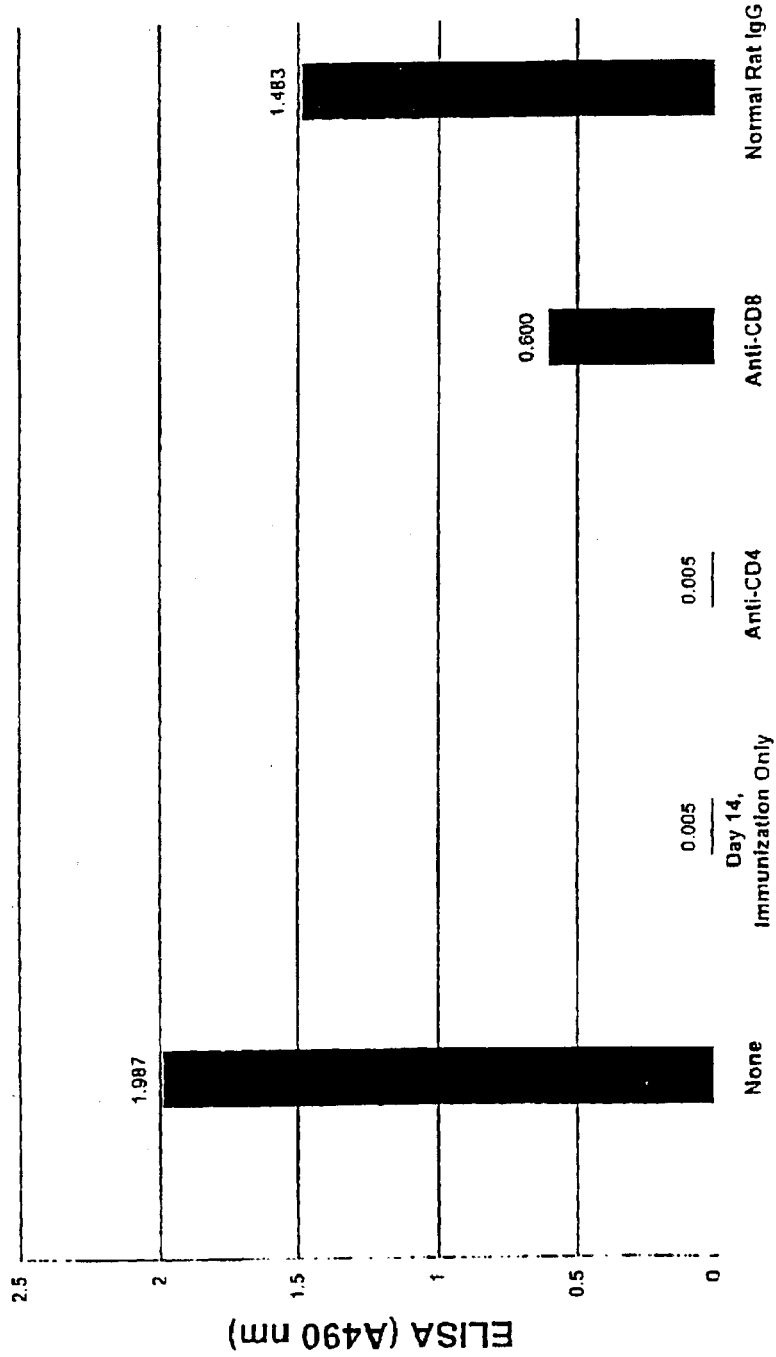

This example is similar to Example 2 but using a more sensitive ELISA test for antibody type. As shown in FIG. 2 the SEQ ID NO:37 antisera depletion was statistically significant (p=0.002) because pretreatment with anti-CD4 completely eliminated any antibodies from being detected at a time when they were detected in control animals (untreated or treated with normal rat IgG). This was not the case, however, with pretreatment using anti-CD8 or normal rat IgG. No antibody data is shown for SEQ ID NO:39, as for this type of MHC-I TCBL construct day 28 is too early to detect any antibodies to the immunogen.

| PEPTIDE CONSTRUCT | Mouse # | IgG1 | IgG2a | IgG2b | IgG3 |
|---|---|---|---|---|---|
| SEQ ID NO: 58 | 4524 | 1.738 | 0.074 | 0.464 | 0.033 |
| | 4525 | 0.123 | 0.005 | 0.017 | −0.013 |
| | 4526 | 1.649 | 0.129 | 0.025 | 0.152 |
| | 4527 | 2.651 | 1.619 | 1.613 | 2.378 |
| | 4528 | 0.562 | 0.047 | 0.059 | 0.000 |
| | 4529 | 0.431 | 0.031 | 0.038 | 0.106 |
| | 4530 | 0.042 | 0.025 | 0.183 | 0.089 |
| | 4531 | 2.391 | 0.200 | 0.123 | 0.358 |
| | 4532 | 1.810 | 0.152 | 0.223 | 0.388 |
| | 4533 | 2.606 | 1.386 | 2.038 | 1.817 |
| | Average | 1.400 | 0.367 | 0.478 | 0.531 |
| SEQ ID NO: 57 | 4534 | 2.577 | 1.399 | 2.050 | 1.853 |
| | 4535 | 2.623 | 1.302 | 1.588 | 1.268 |
| | 4536 | 2.588 | 1.630 | 1.735 | 1.856 |
| | 4537 | 2.601 | 0.467 | 0.534 | 1.229 |
| | 4538 | 2.757 | 1.249 | 1.261 | 2.186 |
| | 4539 | 2.886 | 2.275 | 2.717 | 1.921 |
| | 4540 | 2.768 | 0.998 | 1.656 | 1.276 |
| | 4541 | 2.574 | 1.693 | 2.009 | 2.181 |
| | 4542 | 2.628 | 1.693 | 1.613 | 0.672 |
| | 4543 | 2.671 | 1.566 | 1.785 | 1.183 |
| | Average | 2.667 | 1.427 | 1.695 | 1.562 |
| SEQ ID NO: 62 | 4544 | 0.792 | 0.022 | 0.031 | 0.490 |
| | 4545 | 0.184 | 0.010 | 0.009 | 0.014 |
| | 4547 | 0.742 | 0.323 | 0.610 | 0.597 |
| | 4548 | 0.194 | 0.033 | 0.007 | 0.016 |
| | 4549 | 0.095 | 0.003 | 0.000 | 0.009 |
| | 4550 | 0.072 | 0.003 | 0.008 | 0.041 |
| | 4551 | 0.023 | 0.000 | 0.005 | 0.079 |
| | 4552 | 0.115 | 0.000 | 0.000 | 0.001 |
| | 4553 | 0.095 | 0.007 | 0.000 | 0.016 |
| | Average | 0.257 | 0.044 | 0.074 | 0.140 |
| SEQ ID NO: 63 | 4554 | 0.761 | 0.051 | 0.003 | 0.040 |
| | 4555 | 0.181 | 0.018 | 0.001 | 0.006 |
| | 4556 | 0.649 | 0.020 | 0.007 | 0.104 |
| | 4557 | 0.417 | 0.007 | 0.005 | 0.173 |
| | 4558 | 0.022 | 0.000 | 0.006 | 0.009 |
| | 4559 | 1.379 | 0.000 | 0.028 | 0.013 |
| | 4560 | 0.030 | 0.048 | 0.047 | 0.007 |
| | 4561 | 0.349 | 0.026 | 0.000 | 0.000 |
| | 4562 | 0.717 | 0.192 | 0.027 | 0.058 |
| | 4563 | 2.018 | 0.350 | 0.117 | 0.028 |
| | Average | 0.652 | 0.071 | 0.024 | 0.044 |
| SEQ ID NO: 59 | 4564 | 0.002 | 0.002 | 0.002 | 0.017 |
| | 4565 | 1.603 | 0.027 | 0.014 | 0.032 |
| | 4566 | 0.014 | 0.000 | 0.000 | 0.009 |
| | 4567 | 2.023 | 0.299 | 0.113 | 0.227 |
| | 4568 | 2.199 | 0.060 | 0.039 | 0.324 |
| | 4569 | 0.053 | 0.002 | 0.000 | 0.000 |
| | 4570 | 0.057 | 0.014 | 0.000 | 0.003 |
| | 4571 | 0.505 | 0.011 | 0.000 | 0.016 |
| | 4572 | 0.000 | 0.000 | 0.000 | 0.000 |
| | Average | 0.717 | 0.046 | 0.019 | 0.070 |

| Group | Mouse # | modified HGP-30 | B Clade | C Clade | D Clade | E Clade |
|---|---|---|---|---|---|---|
| SEQ ID NO: 58 | 4524 | 1.740 | 0.000 | 0.047 | 0.001 | 0.000 |
| | 4525 | 0.398 | 0.000 | 0.005 | 0.000 | 0.000 |
| | 4526 | 1.240 | 0.006 | 0.076 | 0.016 | 0.000 |
| | 4527 | 2.665 | 0.230 | 0.643 | 0.000 | 0.504 |
| | 4528 | 1.014 | 0.000 | 0.000 | 0.000 | 0.000 |

-continued

| Group | Mouse # | modified HGP-30 | B Clade | C Clade | D Clade | E Clade |
|---|---|---|---|---|---|---|
| | 4529 | 0.444 | 0.000 | 0.000 | 0.000 | 0.000 |
| | 4530 | 0.304 | 0.000 | 0.000 | 0.000 | 0.000 |
| | 4531 | 1.831 | 0.000 | 0.125 | 0.025 | 0.000 |
| | 4532 | 2.453 | 0.316 | 0.359 | 0.646 | 0.000 |
| | 4533 | 2.530 | 0.148 | 0.238 | 0.000 | 0.016 |
| SEQ ID NO: 57 | 4534 | 2.737 | 1.667 | 1.454 | 1.527 | 0.933 |
| | 4535 | 2.471 | 0.160 | 0.127 | 0.438 | 0.030 |
| | 4536 | 2.569 | 0.099 | 0.427 | 0.408 | 0.113 |
| | 4537 | 2.093 | 0.236 | 0.073 | 0.125 | 0.041 |
| | 4538 | 2.512 | 1.547 | 1.592 | 1.471 | 0.000 |
| | 4539 | 3.115 | 0.470 | 0.651 | 0.772 | 0.029 |
| | 4540 | 3.153 | 1.138 | 1.365 | 1.328 | 0.068 |
| | 4541 | 2.922 | 0.994 | 1.139 | 1.370 | 0.006 |
| | 4542 | 2.236 | 0.000 | 0.008 | 0.000 | 0.000 |
| | 4543 | 2.534 | 0.505 | 1.191 | 0.374 | 0.271 |
| SEQ ID NO: 62 | 4544 | 0.525 | 0.255 | 0.135 | 0.216 | 0.014 |
| | 4545 | 0.137 | 0.016 | 0.014 | 0.000 | 0.000 |
| | 4547 | 1.736 | 0.918 | 0.570 | 1.126 | 0.365 |
| | 4548 | 0.143 | 0.004 | 0.106 | 0.000 | 0.000 |
| | 4549 | 0.077 | 0.006 | 0.055 | 0.007 | 0.000 |
| | 4550 | 0.158 | 0.000 | 0.000 | 0.001 | 0.000 |
| | 4551 | 0.033 | 0.011 | 0.032 | 0.009 | 0.000 |
| | 4552 | 0.121 | 0.013 | 0.068 | 0.000 | 0.000 |
| | 4553 | 0.226 | 0.000 | 0.000 | 0.000 | 0.000 |
| SEQ ID NO: 63 | 4554 | 0.065 | 0.000 | 0.000 | 0.000 | 0.000 |
| | 4555 | 0.216 | 0.282 | 0.135 | 0.012 | 0.000 |
| | 4556 | 0.128 | 0.000 | 0.000 | 0.000 | 0.000 |
| | 4557 | 0.000 | 0.000 | 0.000 | 0.005 | 0.000 |
| | 4558 | 0.110 | 0.000 | 0.000 | 0.000 | 0.000 |
| | 4559 | 0.017 | 0.000 | 0.000 | 0.000 | 0.000 |
| | 4560 | 0.201 | 0.000 | 0.010 | 0.000 | 0.000 |
| | 4561 | 0.623 | 1.977 | 1.878 | 1.941 | 1.565 |
| | 4562 | 0.747 | 0.667 | 0.650 | 0.386 | 0.042 |
| | 4563 | 0.013 | 0.011 | 1.051 | 0.050 | 1.010 |
| SEQ ID NO: 59 | 4564 | 0.440 | 0.262 | 2.421 | 0.120 | 2.431 |
| | 4565 | 0.011 | 0.000 | 1.699 | 0.004 | 1.565 |
| | 4566 | 0.753 | 0.575 | 1.295 | 0.196 | 0.789 |
| | 4567 | 0.905 | 0.026 | 0.969 | 0.000 | 0.788 |
| | 4568 | 0.793 | 0.000 | 0.665 | 0.000 | 0.554 |
| | 4569 | 0.100 | 0.000 | 0.780 | 0.000 | 0.722 |
| | 4570 | 0.035 | 0.000 | 0.171 | 0.000 | 0.142 |
| | 4571 | 0.000 | 0.000 | 1.370 | 0.000 | 1.379 |
| | 4572 | 0.000 | 0.000 | 2.322 | 0.000 | 2.379 |

OF LEAPS MODIFIED HGP-30 IMMUNIZED MICE USING PEPTIDE G OR A DERIVATIZED FORM AS TCBL

| | | Serial Dilution | | | | | |
|---|---|---|---|---|---|---|---|
| Group | Isotype | 1:200 | 1:800 | 1:3200 | 1:12800 | 1:51200 | 1:204800 |
| SEQ ID NO: 58 (with MPL) | Ig1 | 0.103 | 0.022 | 0.003 | 0.000 | 0.000 | 0.000 |
| | Ig2a | 0.248 | 0.048 | 0.000 | 0.000 | 0.002 | 0.000 |
| | Ig2b | 0.147 | 0.026 | 0.022 | 0.006 | 0.007 | 0.018 |
| | Ig3 | 0.265 | 0.044 | 0.006 | 0.001 | 0.000 | 0.000 |
| SEQ ID NO: 57 (with MPL) | Ig1 | 2.642 | 1.638 | 0.652 | 0.279 | 0.091 | 0.014 |
| | Ig2a | 1.961 | 0.899 | 0.263 | 0.081 | 0.028 | 0.005 |
| | Ig2b | 1.872 | 0.881 | 0.253 | 0.104 | 0.011 | 0.006 |
| | Ig3 | 1.965 | 0.805 | 0.215 | 0.045 | 0.005 | 0.000 |
| SEQ ID NO: 58 | Ig1 | 0.507 | 0.173 | 0.025 | 0.009 | 0.014 | 0.000 |
| | Ig2a | 0.000 | 0.015 | 0.000 | 0.003 | 0.006 | 0.000 |
| | Ig2b | 0.017 | 0.000 | 0.004 | 0.001 | 0.000 | 0.000 |
| | Ig3 | 0.009 | 0.002 | 0.000 | 0.000 | 0.000 | 0.000 |
| SEQ ID NO: 57 | Ig1 | 3.006 | 2.441 | 1.755 | 1.069 | 0.367 | 0.114 |
| | Ig2a | 0.729 | 0.218 | 0.068 | 0.025 | 0.015 | 0.008 |
| | Ig2b | 1.420 | 0.505 | 0.134 | 0.054 | 0.014 | 0.000 |
| | Ig3 | 1.132 | 0.358 | 0.092 | 0.020 | 0.004 | 0.000 |
| KLH-m-HGP-30 | Ig1 | 2.693 | 1.582 | 0.621 | 0.294 | 0.065 | 0.000 |
| | Ig2a | 2.276 | 0.980 | 0.330 | 0.115 | 0.015 | 0.003 |
| | Ig2b | 2.284 | 1.069 | 0.344 | 0.169 | 0.018 | 0.009 |
| | Ig3 | 0.903 | 0.235 | 0.040 | 0.003 | 0.001 | 0.000 |

OF LEAPS MODIFIED HGP-30 IMMUNIZED MICE USING PEPTIDE G OR A DERIVATIZED FORM AS TCBL

| | | Serial Dilution | | | | | |
|---|---|---|---|---|---|---|---|
| Group | Isotype | 1:200 | 1:800 | 1:3200 | 1:12800 | 1:51200 | 1:204800 |
| KLH-m-HGP-30 | Ig1 | 3.161 | 2.695 | 1.807 | 1.043 | 0.256 | 0.091 |
| | Ig2a | 2.241 | 1.049 | 0.458 | 0.165 | 0.014 | 0.000 |
| | Ig2b | 2.103 | 0.778 | 0.175 | 0.108 | 0.024 | 0.004 |
| | Ig3 | 0.550 | 0.165 | 0.022 | 0.017 | 0.000 | 0.002 |

| | | Modified | ELISA TEST ANTIGENS | | | |
|---|---|---|---|---|---|---|
| Group | | HGP-30 | B Clade | C Clade | D Clade | E Clade |
| SEQ ID NO: 58 (A) | 4637 | 0.470 | 0.000 | 0.000 | 0.000 | 0.000 |
| | 4638 | 1.103 | 0.000 | 0.000 | 0.000 | 0.000 |
| | 4639 | 0.046 | 0.000 | 0.000 | 0.000 | 0.000 |
| | 4640 | 0.390 | 0.000 | 0.004 | 0.000 | 0.000 |
| | 4641 | 1.297 | 0.028 | 0.104 | 0.000 | 0.000 |
| | 4642 | 0.153 | 0.000 | 0.000 | 0.000 | 0.000 |
| | Group Average | 0.576 | 0.005 | 0.018 | 0.000 | 0.000 |
| SEQ ID NO: 57 (A) | 4643 | 2.307 | 0.271 | 0.616 | 0.052 | 0.092 |
| | 4644 | 1.589 | 0.000 | 0.000 | 0.000 | 0.000 |
| | 4645 | 2.432 | 0.036 | 0.518 | 0.010 | 0.000 |
| | 4646 | 2.867 | 0.507 | 0.920 | 0.000 | 0.018 |
| | 4647 | 2.627 | 0.187 | 0.767 | 0.003 | 0.101 |
| | 4648 | 2.780 | 1.074 | 1.454 | 0.114 | 0.000 |
| | Group Average | 2.433 | 0.346 | 0.712 | 0.030 | 0.035 |
| KLH-m-HGP-30 (A) | 4674 | 3.013 | 2.768 | 2.740 | 0.000 | 0.000 |
| | 4675 | 2.683 | 2.555 | 2.384 | 0.000 | 1.697 |
| | 4676 | 2.774 | 0.842 | 1.545 | 0.012 | 0.135 |
| | 4677 | 2.919 | 2.443 | 2.671 | 0.000 | 0.351 |
| | 4678 | 2.670 | 2.566 | 2.775 | 0.109 | 0.461 |
| | Group Average | 2.749 | 1.920 | 2.138 | 0.025 | 0.446 |
| SEQ ID NO: 58 (B) | 4662 | 0.187 | 0.000 | 0.003 | 0.005 | 0.000 |
| | 4663 | 0.188 | 0.006 | 0.003 | 0.006 | 0.000 |
| | 4664 | 1.848 | 0.000 | 0.000 | 0.000 | 0.000 |
| | 4665 | 0.145 | 0.000 | 0.000 | 0.000 | 0.000 |
| | 4666 | 0.000 | 0.079 | 0.000 | 0.000 | 0.000 |
| | 4667 | 0.000 | 0.046 | 0.050 | 0.000 | 0.000 |
| | Group Average | 0.394 | 0.022 | 0.009 | 0.002 | 0.000 |
| SEQ ID NO: 57 (B) | 4668 | 2.330 | 2.348 | 2.575 | 0.087 | 0.000 |
| | 4669 | 2.213 | 0.496 | 0.837 | 0.095 | 0.000 |
| | 4670 | 2.534 | 1.799 | 1.711 | 0.185 | 0.054 |
| | 4671 | 3.358 | 1.228 | 2.254 | 1.799 | 0.358 |
| | 4672 | 3.030 | 2.244 | 0.911 | 1.727 | 0.113 |
| | 4673 | 2.571 | 0.349 | 1.070 | 0.637 | 0.037 |
| | Group Average | 2.672 | 1.410 | 1.559 | 0.755 | 0.094 |
| KLH-m-HGP-30 (B) | 4679 | 2.852 | 2.546 | 2.317 | 1.648 | 0.054 |
| | 4680 | 3.484 | 1.243 | 2.006 | 0.094 | 0.000 |
| | 4681 | 3.374 | 2.622 | 2.873 | 0.000 | 1.094 |
| | 4682 | 3.262 | 2.485 | 2.863 | 0.324 | 0.000 |
| | 4683 | 3.009 | 2.554 | 2.623 | 1.383 | 1.044 |
| | Group Average | 3.109 | 2.143 | 2.373 | 0.700 | 0.381 |

| | | A 490 1:200 dilution on plates coated with | | |
|---|---|---|---|---|
| Group | Animal # | modified HGP-30 | Peptide G | KLH |
| SEQ ID NO: 58 | 4637 | 0.257 | 0.195 | ND |
| | 4638 | 0.571 | 0.122 | ND |

-continued

| Group | Animal # | modified HGP-30 | Peptide G | KLH |
|---|---|---|---|---|
| | 4639 | 0.065 | 0.092 | ND |
| | 4640 | 0.392 | 0.088 | ND |
| | 4641 | 1.008 | 0.054 | ND |
| | 4642 | 0.021 | 0.047 | ND |
| | Average | 0.386 | 0.099 | |
| SEQ ID | 4643 | 2.178 | 0.083 | ND |
| NO: 57 | 4644 | 1.411 | 0.054 | ND |
| | 4645 | 2.314 | 0.097 | ND |
| | 4646 | 2.555 | 0.038 | ND |
| | 4647 | 2.404 | 0.087 | ND |
| | 4648 | 2.273 | 0.121 | ND |
| | Average | 2.189 | 0.080 | |
| KLH-m-HGP-30 | 4674 | 2.825 | 0.248 | >3.5 |
| | 4675 | 2.724 | 0.186 | >3.5 |
| | 4676 | 2.544 | 0.303 | >3.5 |
| | 4677 | 2.862 | 0.185 | >3.5 |
| | 4678 | 2.654 | 0.150 | >3.5 |
| | Average | 2.722 | 0.214 | >3.5 |

-continued

A 490 1:200 dilution on plates coated with

| Group | Animal # | modified HGP-30 | Peptide G | KLH |
|---|---|---|---|---|
| SEQ ID | 4662 | 0.051 | 0.024 | ND |
| NO: 58 | 4663 | 0.052 | 0.044 | ND |
| | 4664 | 1.102 | 0.062 | ND |
| | 4665 | 0.005 | 0.033 | ND |
| | 4666 | 0.000 | 0.060 | ND |
| | 4667 | 0.000 | 0.151 | ND |
| | Average | 0.202 | 0.062 | |
| SEQ ID | 4668 | 1.968 | 0.091 | ND |
| NO: 57 | 4669 | 1.422 | 0.024 | ND |
| | 4670 | 1.755 | 0.006 | ND |
| | 4671 | 2.450 | 0.015 | ND |
| | 4672 | 2.403 | 0.126 | ND |
| | 4673 | 1.399 | 0.113 | ND |
| | Average | 1.899 | 0.062 | |
| KLH-m-HGP-30 | 4679 | 2.701 | 0.171 | >3.5 |
| | 4680 | 2.177 | 0.057 | >3.5 |
| | 4681 | 2.397 | 0.167 | >3.5 |
| | 4682 | 2.489 | 0.028 | >3.5 |
| | 4683 | 2.108 | 0.032 | >3.5 |
| | Average | 2.374 | 0.091 | >3.5 |

TABLE 6

DETERMINATION OF TYPE OF CELLS INVOLVED IN DTH RESPONSE TO MODIFIED HGP-30 BY LEAPS IMMUNIZED MICE BY ANTISERA DEPLETION OF CD4 OR CD8 CELLS

| | | Treatment* | | | | | |
|---|---|---|---|---|---|---|---|
| | | SEQ ID NO: 57 (with MHC II TCBL for CD4) | | | SEQ ID NO: 58 (with MHC I TCBL for CD8) | | |
| DTH Parameters Ear inoculated day 26 with Ear thickness measured after 48 hours | | Right Ear saline mm | Left Ear HGP-30 mm | % increase (L-R)/R | Right Ear saline mm | Left Ear HGP-30 mm | % increase (L-R)/R |
| None | Average of group (5 mice) | 0.224 | 0.274 | 22.10% | 0.222 | 0.288 | 29.30% |
| Normal rat IgG | Average of group (5 mice) | 0.232 | 0.278 | 19.90% | 0.227 | 0.296 | 30.60% |
| Anti CD4 | Average of group (5 mice) | 0.237 | 0.252 | 6.10% | 0.240 | 0.288 | 20.00% |
| Anti CD8 | Average of group of 5 mice | 0.232 | 0.290 | 25.00% | 0.220 | 0.233 | 6.20%*** |
| Day 14** Injection Only | Average of group of 5 mice | 0.222 | 0.234 | 5.10% | 0.231 | 0.254 | 10.00% |

*animals were treated with antisera daily for 5 days before initiation of immunizations on days 1 and 14 with LEAPS construct and ISA 51 adjuvant

**animals were only immunized with LEAPS construct on day 14

***t test $p < 0.05$

What is claimed is:

1. A peptide having the sequence of SEQ ID NO:1.

2. A peptide construct capable of eliciting a cellular immune response when administered to a patient in need thereof, said peptide construct comprising a first T cell specific binding peptide and a second T cell specific binding peptide, said first and second peptides being derived from different molecules and covalently linked together, wherein said first T cell specific binding peptide binds to a specific class or subclass of T cells and has the sequence of SEQ ID NO:1, and said second T cell specific binding peptide is an antigenic peptide capable of eliciting TH1 associated antibodies, and wherein said first and second peptides are covalently linked to each other directly or via a spacer.

3. The peptide construct of claim 2 wherein the antigenic peptide is a peptide having sequence identity with the p17 gag protein of HIV-1 wherein the peptide has a sequence originating with an amino acid residue chosen from residues chosen from residues 76 to 83 and ending with an amino acid residue chosen from residues 107 to 112 of p17 gag protein of HIV-1.

4. The peptide construct of claim 3 having SEQ ID NO:37.

5. An immunogenic composition comprising the peptide construct of claim 2 or 3 and an immunogenic carrier.

6. An immunogenic composition comprising the peptide construct having SEQ ID NO:37 and an immunogenic carrier.

7. A method of eliciting a cellular immune response in a human patient in need thereof, comprising administering to said patient an immunologically effective amount of the peptide construct of claim 2 or 3.

8. The method of claim 7 wherein the peptide construct is administered in combination with an immune response adjuvant.

9. A method of eliciting a cellular immune response in a human patient exposed to or at risk for exposure to the AIDS virus, comprising administering to said patient an immunologically effective amount of a conjugated peptide having SEQ ID NO:37.

* * * * *